US006635614B1

(12) United States Patent
Santamarina-Fojo et al.

(10) Patent No.: US 6,635,614 B1
(45) Date of Patent: Oct. 21, 2003

(54) USE OF LECITHIN-CHOLESTEROL ACYLTRANSFERASE (LCAT) TO REDUCE ACCUMULATION OF CHOLESTEROL

(75) Inventors: Silvia Santamarina-Fojo, Potomac, MD (US); Jeffrey M. Hoeg, Potomac, MD (US); H. Bryan Brewer, Jr., Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/068,386

(22) PCT Filed: Nov. 8, 1996

(86) PCT No.: PCT/US96/18159

§ 371 (c)(1),
(2), (4) Date: Nov. 22, 1999

(87) PCT Pub. No.: WO97/17434

PCT Pub. Date: May 15, 1997

Related U.S. Application Data

(60) Provisional application No. 60/006,400, filed on Nov. 9, 1995.

(51) Int. Cl.$^7$ ............................................. A61K 38/00
(52) U.S. Cl. ..................... 514/2; 435/69.1; 435/320.1
(58) Field of Search .................. 435/68, 172.3, 435/69.1, 320.1; 514/2

(56) References Cited

U.S. PATENT DOCUMENTS

| | | | | |
|---|---|---|---|---|
| 4,943,527 A | * | 7/1990 | Protter et al. | 435/69.6 |
| 5,049,488 A | * | 9/1991 | Baer et al. | 435/6 |
| 5,721,114 A | * | 2/1998 | Abrahamsen et al. | 435/69.1 |
| 5,733,879 A | * | 3/1998 | Rosseneu et al. | 514/13 |

FOREIGN PATENT DOCUMENTS

| | | |
|---|---|---|
| DE | 41 28 288 A | 3/1993 |
| EP | 0 222 591 A | 5/1987 |
| WO | WO 87/02062 | 4/1987 |
| WO | WO 95/25793 | 9/1995 |
| WO | WO 96/28553 | 9/1996 |

OTHER PUBLICATIONS

Wu–Pong et al. Biopharmaceutical drug design and development pp. 204–238 1999.*
Stedronsky Interaction of bile acids and cholesterol with non–systemic agents having hypocholesterolemic properties pp. 255–287 1994.*
Luc et al. Les hypoalphalipoproteinemies sont–elles toujours un facteur de risque de l'atherosclerose? 205–212 vol.9, 1997.*
Ribalta et al. Evidence against alterations in lecithin:cholesterol acyltransferase (LCAT) activity in familial combined hyperlipidemia pp. 383–389 1998.*
Mehlum et al. Overexpression of human lecithin:cholesterol acyltransferase in mice offers no protection against diet–induced atherosclerosis pp. 336–342 2000.*
Stein et al. Atheroprotective mechanisms of HDL pp. 285–301 1999.*
Liu et al. Specificity of lecithin:cholesterol acyltransferase and atherogenic risk: comparative studies on the plasma composition and in vitro synthesis of cholesteryl esters in 14 vertebrate species vol.36, 1995 pp. 1813–1824.*
McNamara et al. Dietary cholesterol and atherosclerosis pp. 310–320 2000.*
Ueno et al. selectivity and contribution of lecithin: Cholesterol acyltransferase to plama cholesterol ester formation 1 vol.99,No. 2, 1986.*
Assmann G. et al. HDL metabolism and atherosclerosis Journal of Cardiovascular Pharmacology, 1991 16/suppl. 9 (15–s20) ISSN 0160–2446 coden: JCPCDT.*
Stedronsky E. R. Interaction of bile acids and cholesterols with non–systemic Biochimica et Biophysica Acta–Lipids Metabolism, 1994 1210/3 (255–287).*
Verma, Gene therapy: Beyond 2000, 2000, Molecular Therapy, vol. 1, p. 493.*
Buckel, Recombinant proteins for therapy, 1996, TiPS, vol. 17, pp. 450–456.*
Chawla, D et al. secretion of active human lecithin–cholesterol acyltransferase by insect cells infected with a recombinant baculovirus, Biochem. J. (1995) 399, 249–253.*
Crystal, R. Transfer of Genes to Humans: Early lessons and Obstacles to success: Science vol 270, Oct. 20, 1995.*
Verma et al. :Gene Therapy—promises, problems and prospects, Nature vol 389, Sep. 1997, p. 239–242.*
Orkin, et al. :Report and Recommendations of the Panel to Assess the NIH Investment in Research on Gene Therapy, www.nih.gov Dec. 1995.*
International Search Report.
J. McLean, et al., "Human lecichin–cholesterol acyltransferase gene: complete gene sequence and sites of expression," *Nucleic Acids Research* 14(23):9397–9406 (1986).
Klein, et al., "Two Different Allelic Mutations in the Lecithin–Cholesterol Acyltransferase Gene Associated with the Fish Eye Syndrom," *J. of Clin. Investigation* 89:499–506 (1992).
McLean, et al. "Cloning and expression of human lecithin–cholesterol acyltransferase cDNA," *Proc. Natl. Acad. Sci. USA* 83:2335–2339 (1986).

(List continued on next page.)

*Primary Examiner*—Dave T. Nguyen
(74) *Attorney, Agent, or Firm*—Townsend and Townsend and Crew LLP

(57) ABSTRACT

This invention provides methods for treating atherosclerosis in a mammalian subject by increasing the activity of LCAT in the serum of the subject to a level effective to decrease the accumulation of cholesterol in the subject. Pharmaceutical dosage forms containing LCAT also are provided.

8 Claims, 12 Drawing Sheets

OTHER PUBLICATIONS

Gordon, et al., "High–Density Lipoprotein—The Clinical Implications of Recent Studies," *N. Engl. J. Med.* 321(19):1311–1316 (1989).

Gordon, et al., "High–density lipoprotein cholesterol and coronary heart disease in hypercholesterolemic men: The Lipid Research Clinics Coronary Primary Prevention Trial," *Circulation* 74(6):1217–1225 (1986).

Glomset, et al., "Role of plasma lecithin: cholesterol acyltransferase in the metabolism of high density lipoproteins," *J. Lipid Res.* 7:638–648 (1966).

Glomset, "The plasma lecithin:cholesterol acyltransferase reaction" *J. Lipid Res.* 9:155–167 (1968).

Mehlum, et al., "Tissue–specific expression of the human gene for lecithin: cholesterol acyltransferase in transgenic mice alters blood lipids, lipoproteins and lipases towards a less atherogenic profile," *Eur. J. Biochem.* 230:567–575 (1995).

Hoeg et al., "Overexpression of human lecithin–cholesterol acyl transferase in transgenic rabbits leads to hyperalpha–lipoproteinemia" *Atherosclerosis* 109(1,2):11 (1994).

Hoeg et al., "Lecithin–Cholesterol Acyl Transferase Transgenic Rabbits: Hyperalphalipoproteinemia and Diet–Induced Atherosclerosis," *Circulation* 92(8):1707 (1995).

* cited by examiner

LCAT Transgenics (n = 9)
5% ± 1%*

Controls (n = 10)
35% ± 7%

0-10  10-20  20-30  30-40  40-50    50+

Control            Transgenic

CONTROL AND LCAT TRANSGENIC RABBITS

FIG. 5A.

```
   1  CTGCAGACATGGAGTTCCTCGAGGTGCTGACCGAGGGCCTTGAGCGGGTGCTGTTGGTGCGCGGTGGTGCCGTGAAGTCATCA
  85  CCATCTACTCCTGAGCCCAGTGTCATCTTGTGCCTGGAGTCGAGGTCTTGGCCAGGACATAACAAGCTGTGGTCTGGGGTAAC
 169  AGCCTCTTCCCAGCACCCACCTGCCAGCCCTGTCCTGCCTTGCCCTGGACCCCAGTTGCTAGTCTCCTTGGAAACCAG
 253  GCCTGGGCCTCAAAATGGAGATGGATCCCAGGTCTTGTGGGACCCTGGGACTTTACTATCTAGCACCCCAGTAG
 337  GCCTGTCCTGGCCAGAGAAGACTGGGGTTTGAAGGCAGCCCGGCGGAGGAGTCCAGCCCAGCTGCCTGCAGGAA
 421  TGCATATTTATTGTTTGGATGTCACCATCAGAGACGAAGGGAAGGGTAGCCAGGACCGAATGGAGACCAGCTGAGGCCTGACTTTTCAA
 505  GATCTGGCTCAGTCTACTATGGGCAGGGCCTCCTGCCCCGGCTCTGTTCCCCTGCCCGCCAAGAGAAGGGGAACTGAACCCAG
 589  TAAAACATTGTGTAGTTCTGGGCCTGTGCCCCAGGCCGTCCCCTCCCCACTG
 673  GCCCAGAGCCGGCTCCCCTGAGGCTGCCCCAGTGCCGTTTCTCTGGCAGTAGGCACCAGGGCTGGAATGG
                                                                          ▶ exon 1           MetG
 -24
 757  GCCCTAGGGCCCCCACTCCCCACACCAGATAAGGACAGCCCAGTGCCGTTTCTCTGGCAGTAGGCACCAGGGCTGGAATGG
      lyProProGlySerProTrpGlnTrpValThrLeuLeuLeuGlyLeuLeuLeuProProAlaAlaProPheTrpLeuLeuAsnVal
 -23
 841  GGCCGGCCCGGCTCCCCATGGGTCAGCAGTGGGTGCTGGGGCTGCTGCTCCCCGCCGCCCCTTCTGGCTCCTCAATG
       7  LeuPheProProHisThrThrProLysAlaGluLeuSerAsnHisThrArgProValIleLeuV
 925  TGCTCTTCCCCCCGCACCACGGCCAGGCTGAGCTCAGTAACCACACGGCCCGTCATCCTCGGTAAGCCCCACCAGGCC
1009  CCTGATGCACCACGCCAGACCCTGGGGAGCCTGGGCAGCTGACCTGGCCAAAGCCCTTCTGCCCTGCATAA
```

```
1093  GCCCCGACATAAGTACCTGCCCTGGTGTGGGAGGGGCCAAAAGCTTGTCCCTTAGAGGAATGACGTCCCTTCTCCCACCACAC
1177  TGTGACTCTCAGTGTCTAACCCAGGGGGGGGGAGTGGGGGACGGGGTGTGCCTGAGGTCTTGGCTGGGCATCACAAGCTGTG
1261  GTCAGTCACAGCCACACCAGACTCTGGGCACCACACTCCTTCCTTGGCCCCCACCAAGGACAAGATGCCCAGCCC
1345  AGGATCGGTGAGCAGGAGAGGCCCATCCATGCCCGGCCCCCAGCCCCCATGCCCAGCCAGGGTCAGCGGCCTTGGCCTCAGCACCTCAG
1429  TTGGACTTTGGCAATAAAGGAGCCCAGACTGGGCTTTGCTCTCTGCAGAGGCAGGGAGACAGCAGGGAGGGGTGTAAGCAGGGAGGGTAAGTG
1513  CGCCTTCCCTCCTCAGGGAAGCCTGGGCTTTGGCTACTGGGGGACAGCAGGGGTCTGCACTGCAGCATCTGGGTGACGGGGTAAGGGTC
1597  TGCTTTGTACCTGGGGGTTGAGGGTATGGGGAGGTGGGGGTGGGTCACTGCAGCATCTGGGTGACGGGGTAAGGGTC
                                                                      exon 2  alProGlyCysLeuGlyAsnGlnLeuGluAlaLysLeuAsp
1681  ACGGGGGAATCCAGAGTCCAGAGTGAGGGCTGCTCACAGTGCCCGGCCTGGGAATCAGCTAGAAGCCAAGCTGGAC
         LysProAspValValAsnTrpMetCysTyrArgLysThrGluAspPhePheThrIleTrpLeuAspLeuAsnMetPheLeuPro
42
1765  AAACCAGATGTGGTGAACTGGATGTGCTACCGCAAGACAGAGGACTTCTTCACCATCTGGCTGGATCTCAACATGTTCCTACCC
         LeuGlyValAspCysTrpIleAspAspAsnThrAr
70
1849  CTTGGGGTAGACTGCTGGATCGATAACACCAGGTACAGCCATGTGCTCCACCCTAGCCCCAACACGCTGCCCCTTGGCTACTGG
                                          exon 3  gValValTyrAsnArgSerGlyLeuValSerAsnAlaProGlyValGlnIleArg
81
1933  CTGCTGAGTGGCACCCCCGCCAGGGTTGTCTACAACCGGAGCTCTGGGCTCGTGTCCAACGCCCCTGGTGTCCAGATCCG
         ValProGlyPheGlyLysThrTyrSerValGluTyrLeuAspSerLysLeuAlaG
100
2017  CGTCCCTGGCTTTGGCAAGACCTACTCTGTGGAGTACCTGGACAGCAAGCTGGCAGGTTTGTGTCAGAGGGCAGGGCTGGG
```

```
                                                         exon 4  lyTyrLeuHisThrLeu
120
2101 GCTCCAGGCCTGGGTGCTGGCCCACAGCAGGCATGGCCCAAGCCCCCGGTGTCTGCTGGTCCCCCACAGGGTACCTGCACACAC ValGlnAsnLeuValAlaAsnGlyTyrValArgGluThrValAlaArgAlaAlaProTyrAspTrpArgLeuGluProG
125
2185 TGGTGCAGAACCTGGTCAACAATGGCTACGTGCGGGACGAGACTGTGGCGCGCGCCGCCCCTATGACTGGCGGGCTGGAGCCCGGTG exon 5  lyGln
151
2269 AGTGTCTCTGCGGATGACCGGCTTGGGGTGGGGCAGGTGCCCCAGACCCCAGCTGCCCTGACCCCTTCCACCCGCTGCAGGCCA GlnGluGluTyrTyrArgLysLeuAlaLeuAlaGlyLeuValGluGluMetHisAlaAlaTyrGlyLysProValPheLeuIleGlyHis
153
2353 GCAGGAGGAGTACTACCGCAAGCTCGCAGGGCTGGTGGAGGAGATGCACGCTGCCTATGGGAAGCCTGTCTTCCTCATTGGCCA SerLeuGlyCysLeuHisLeuLeuTyrPheLeuLeuArgGlnProGlnAlaTrpLysAspArgPheIleAspGlyPheIleSer
181
2437 CAGCCTCGGCTGTCTACACTTGCTCTATTCCTGCTGCGCCAGCCCCAGGCCTGGAAGGACCGCTTTATTGATGGCTTCATCTC LeuGlyAlaProTrpGlyGlySerIleLysProMetLeuValLeuAlaSerG
209
2521 TCTTGGGGCTCCCTGGGGTGGCTCCATCAAGCCCATGCTGGTCTTGGCCTCCAGGTGAGAAGGCCTCGAACACTTAGGTCCAGCG 2605 ATGGGTGAGACCAAGCTGATCCTGGGCTCCTGCCTTCATTGCGGCTCCTGCTCACAGTGGCCTCTAGGGGTGCTATCTACCACTCC 2689 TGGGCTGGCATGCTTGCTGTGCTCACTGGCCCCCAGAGCAGTGACCCTGGCCTGAGCAATTAGGGTGGCCTCCTTCCAGAGTCTGTGT 2773 CAGTGATGGCAAAGGGGCAGTGAACACAGAAAGTGAATCCCAGCTATCTGCTCCCAGGGTTTGTTCTTGTAGCCCCAGAGCCTG 2857 CCTGCCCAGCCCTTGCCTGCTTCCACTTGCTCGCAGGAGTGCCTTGCCCAGGGATGTGCTTCACTGAGGATGGATCTGCCAG 2941 AGCTAGGGCCAGACCCCGAGGCCCACCTGCTCTTCCCTAGGAGTGCACCAGGCCACCAGCACTGACAAGAAACGCTCATCAGACACCACCTA 3025 CTCCCCACCCCCTGTACCCTGGGAGCTGGTCTGGAGAGAGAAACACAGTCTGGACAAGAGAAACGCTCATCAGACACCACCAAT
```

```
3109  AAACATCAAACAGACACCATCTTGTTCCCCCTTTCTGGAGCACAACTCTGTGGCCCCCATTGCTGCATAAGCCACACAAGGAG
3193  CAGAAAGACACATGCCCGAGGAGGAGACAGCCAGCACCGCCCCCACACATCCCCACCATCCTGGGCCTCACCCACCATCCCCACA
                                                Alu SEQUENCE
3277  CACCCCTGGTCCTCAGGAAGCCCCGCCTACTTTTTTTTTTTTCAGACAGGTCATTCTGTCGCCCAGGCTGGAGTGCAGTG
3361  GCGTGATCATAGCCGCAGTCTCAATCTCCCTGCCCAAGCAATCCTCCTGCCTCAGCCTCCTGGTTAGCTGAGACTATAGGCAC
3445  ACAACACCACCACCTAATTTATTTTGTTTTTTAGTAGAGATGAGGTCTTGCTATGTTGCCCAGGCTGGTCTCAAACTCTTCACC
                                                                                   Alu
3529  TTAAGTGATCTTCCTGCCTCAGCCTCCCAAGTGCTGGGATTACAGGCGTGAGCTACTGTGCTGGGCCTTTTAAAAAATCTTTA
      SEQUENCE
3613  TTTGTTTATTATTTGAGATGGAGTCTCGCTCTGTTTCCCAGGCTGGAGTGCAGTAGTGCAATCTCCACTCACTGCAAC
3697  CTCCATCTCCCCAGTTCAAGTGATTCTTCTGCCTCAGCCTCCCAGTAGTAGGATCACAGGCATGTGCCACCACGCCCTGGCTA
3781  ATTTTTATATATTTTAGTAGAGATTAGGTTTCCCCATGTTGGCCAGGCTGGTCTCGAACTCCTGACCTTAAGTCATCTGCCTGCC
                                                                  Alu SEQUENCE
3865  TCGGCCTCCCAAAGTGCTAGGATTACAGGTGTGAGCCACCGTACCCGGCCCTATTTATTTATTTTTAAGCTGAATCTCACTG
3949  TGTCACCCAGGCTACAGTGCAGTGGTGCGATCATAGTTTACTGTAACCTCAAATTCCTAGGCTCAAGCAATCTTCCTGCCTTTG
4033  CCTCCTGAGTAGCTAGGACTAGAGGTGCACTCCACTAAGCCCAGCTGATTTTTTTTTTTTTGTAGAGACAGGGTCTC
4117  ACTGCATTGCCTAGTCTGGTCCTGTCCCTGCCATCCTTTGAAGCCCTCAAGTGATCCTTATCAGGCCTCCAAAGTGTTGGATTACAGGGG
4201  TGAGCCATGGTGCCTGCCTACGACTCCTTTGAAGCCCTACAGCTCCACCCAACAGAGGTCTTATCAGGCTTCCTCATTGAGT
4285  AAGCTGACACTGAGCATCATTGAATATCAGGCCTGCTCAAGCCTGTGGCTTAGAGTCTGTGTCTAGATTGGGCAGGGACAAGAT
```

FIG. 5D.

```
                                                                                   exon 6
4369  TGAGCATCTGGCTGAGCCTACACTCAGCAGGTTGTGGGCCAGGGCCTGGCTCCCTGTCCCCACTTGCTCCATATC
227         lyAspAsnGlnGlyIleProIleMetSerSerIleLysLysGluGlnArgIleThrThrSerProTrpMet
4453  CACAGGTGACAACCAGGCATCCCCATCATGTCCAGCATCAAGCTGAAAGAGGAGCAGCGCATAACCACCACCTCCCCCTGGAT
253   PheProSerArgMetAlaTrpProGluAspHisValPheIleSerThrProSerPheAsnTyrThrFlyArgAspPheGlnArg
4537  GTTCCCTCTCGCATGGCCTGGCCTGAGGACCACGTGTTCATTTCCACACCCAGTTCAACTACACAGCCGTGACTTCCAACG
281   PhePheAlaAspLeuHisPheGluGluGlyTrpTyrMetTrpLeuGlnSerArgArgAspLeuLeuAlaGlyLeuProAlaProGly
4621  CTTCTTTGCAGACCTGCACTTTGAGGAAGGCTGGTACATGTGGCTGCAGTCACGTCGTGACCTGCTGGCAGGACTCCCAGCACCTGG
309   ValGluValLeuTyrCysLeuTyrGlyValGlyLeuTyrGlyValGlyLeuProThrProArgThrThrTyrIleTyrAspHisGlyPheProTyrThrAspPro
4705  TGTGGAAGTATACTGTCTTTACGGCGTGGGCCTGCCCACGCCCCACGCACCTACATCTACGACCACGGCTTCCCCTACACGGACCC
337   ValGlyValLeuTyrGluAspGlyAspAspThrValAlaThrArgSerThrGlyLeuCysGlyLeuTrpGlnGlyArgGlnPro
4789  TGTGGGTGTGCTCTATGAGGATGGTGATGACACGGTGGCAACCCGCAGCACCGGCCTCTGTGGCCTGTGGCAGGGCCGCCAGCC
365   GlnProValHisLeuLeuProLeuHisGlyIleIleGlnHisLeuAsnMetValPheSerAsnLeuThrLeuGluHisIleAsnAla
4873  ACAGCCTGTGCACCTGCTGCCCCTGCACGGGATACAGCATCTCAACATGGTCTTCAGCAACCTGACCCTGGAGCACATCAATGC
393    IleLeuLeuGlyAlaTyrArgGlnGlyProAlaSerProThrAlaSerProGluProProProGluEnd
4957  CATCCTGCTGGGTGCCTACCGCCAGGGTCCCGCTAGCCCCACTGCCAGCCCCGACTCCCCGAGCCCCGCCTCCCTGAATAAAGACCTTC
5041  CTTTGCTACCGTAAGCCCTGATGGCTATGTTTCAGGTTGAAGGGAGGCACTAGAGTCCCACACTAGGTTTCACTCCTCCACCAGC
5125  CACAGGCTCAGTGCTGTGTGCAGTGAGGCAAGATGGGCTCTGTGAGGCCTGGGACTGAGCTGGGCACCCTAGAGATGTACAGCTG
5201  CCCACTCTCCTGGTTGCTCGAGCTGTTGAGGCAGTGTGCACCGTGCCTCCTGTGCTGGGCGCGGGGACTGGAGCTGGCTCCACCC
```

FIG. 5E.

```
5293  ACAGCCCTGTCAGAGGAGCACGGGGCGGTGGGGGGCGGTGACAATTTGAGCTGTCTCTCCCAGCTCCCAAAAGGGCAGGTGAG
                                                  Alu SEQUENCE
5377  ACGACCTTTGAGTGCTGGGTGATGACAGGGCCACAAGTGTTTAGAGGCCGGGCACGGTGGCTCACGCCTGTAATCCTGCAC
5461  TTTGGGAGACCGAGGCAGGCGGATCACCTGAACTCAGGAGTTTGAGACCAGCCAGGCCAACATGGCAGAAACCCCGTCTCTAC
5545  TAAAATACAAAATATTGCCAGGCGTGGTGGCGCATGCCTGTCGTCCCAGCTACTCAGGAGGCTGAGGCACGAGAATCATTTCA
5629  ACCTGGGAGGTGAGGTCACTGTGAGCCGAGATCACGTCGTTGCACTCCAGACTGGGCGGCAGAATGAGACTGTCTCAAAAAAA
5713  AGAGACTGGGTCTCAAAAAAAAAAAAAGTTAGAATTAAAATCTGGAGTGACAACCATTAATCAGATCATTTCAC
                                                                            Alu
5797  TAATGGAAGTTTAATTACTAATGAAGCTAAATGCTCTGAGAAAAGCTTAGGAAGCACAAGAGGCTGAGCCTTTCAGGTCAGCAA
5881  AGACTTCCCAGGAGGCAGTGCCTACACTGAGGTCAGAGTGACAAGAGTAATGGACCACTGTAAAGACTTGGGTTCGGCC
      SEQUENCE
5965  GGGCGCGGTGGCTCACGCCTGTAATCCCAGCACTTTGGGAGGCCGAGGTGGATCATGAGGTCAGGAGATCGAGACCATCC
6049  TGGCTAACAAGGTGAAACCCCGTCTCTACTAAAAATACAGAAAATTAGCCGGGCGTGGTGGCGGGCGCCTGTGGTCCCAGCTAC
6133  TCGGGAGGCTGAGGCAGGAGAATGGCGTGAACCCGGGAGGCTTGCAGTGAGCCGAGATTGCGCCACTGCAGTCCGCAGT
6217  CCGGCCTGGGCGACAGAGCGAGACTCCGTCTCAAAAAAAAAAAAAAGACTTGGTTTGACTTGATTGAGCCCAGGAGTTCGAGAC
                                                                Alu SEQUENCE
6301  AAGCCTGGGCAATATAGTGAGACCTCATCTCTACAAAAATTTAAAAATTAGCCTGGTGCGGTGGCTCATGCCTGTAATCCCAG
6385  CACTCTGGGAGGCCGAGGTGGGCGGATCACTTGAGGTCAGAAGTTTGAGACCACCCTGACCAACATGGAGAAACCCCGTCTCT
6469  ACTAAAAATACAAAATTAGCCGGGCGATGGTGGCGCATGCCTGTAATCCCAGCTACTCGGGAGGCTGAGGCAGGAGAATTGTTTG
```

*FIG. 5F.*

6553 AACCTGGGAGGTGGACGTTGCGGTGAGCCAAGATCACACTATTGCACTCCAGCCTGGGCAACAAGAGCAAAACTCCGTCTCAAA
            Alu SEQUENCE
6637 AAAAAAAATTTATTTTTAAATTAGCCAGGTGTAGTCAAATCTACTAGGCAGCTGTGAGTGGGAGGATTGCTT
6721 GAACCTGGGAGGCAGAGGTTGCAGTGAGCCAAGATGGTGCCACGGCATTCCAGCCTGAGCAACAGCAAGACCCTGTGTCCAAAA
6805 AAAAAAAAAAAAAACCGTAAAATAGGCCAGGCACAGTGGTTCATGGTTATAAGCCTAGCACTTTGGAAGGCTGAGGAGGGTG
6889 GATCGCCTGAGCTC

*FIG. 5G.*

USE OF LECITHIN-CHOLESTEROL ACYLTRANSFERASE (LCAT) TO REDUCE ACCUMULATION OF CHOLESTEROL

This is a U.S. national phase of PCT/US96/18195, filed Nov. 8, 1996, which claims priority to U.S. provisional application No. 60/006,400, filed Nov. 9, 1995.

BACKGROUND OF THE INVENTION

This invention relates to methods for the prophylactic and therapeutic treatment of atherosclerosis and to diseases relating to a deficiency in lecithin-cholesterol acyltransferase activity.

Atherosclerosis is a pathological condition of mammals characterized by the accumulation of cholesterol in the arteries. Cholesterol accumulates in the foam cells of the arterial wall, thereby narrowing the lumen. This results in decreased flow of blood. The clinical sequelae of atherosclerosis include heart disease and heart attack, stroke, and peripheral vascular disease. Together, these diseases account for more disease-related deaths in industrialized countries than any other cause.

The development of human atherosclerosis is inversely related to the concentration of high density lipoproteins (HDL) in the serum. D. J. Gordon and B. M. Rifkind (1989) *N. Engi. J. Med.* 321:1311. High concentrations of HDL appear to protect against the development of premature atherosclerosis, while low HDL cholesterol concentrations are associated with an increased risk of cardiovascular disease. D. J. Gordon et al. (1986) Circulation 74:1217. It has been proposed that a 1% increase in the concentration of HDL would lead to a 3% reduction in risk for developing clinical atherosclerosis in man. Gordon and Rifkind, supra.

The plasma protein enzyme lecithin-cholesterol acyltransferase (LCAT) catalyzes the transfer of fatty acid from the sn-2 position of lecithin to the free hydroxyl group of cholesterol. J. A. Glomset et al. (1966) *J. Lipid Res.* 7:638). J. McLean et al. (1986) *Proc. Nat'l. Acad. Sci. USA* 83:2335–2339 described the cloning and sequence of a human LCAT cDNA. J. McLean et al. (1986) *Nucl. Acids Res.* 14:9397–9406 described a complete gene sequence for human LCAT.

It was first proposed nearly 30 years ago that the esterification process with this enzyme could be the key step in transferring cholesterol from the tissues of the body to the liver. This process, termed "reverse cholesterol transport" (J. A. Glomset (1968) *J. Lipid Res.* 9:155), was proposed to facilitate the removal of cholesterol from the body. However, increases in LCAT were not known to diminish the risk of atherosclerosis.

Various mutations of the LCAT gene are known. Individuals who are homozygous for a non-functional LCAT mutant have classic LCAT deficiency disease, characterized by clouding of the cornea, normochromic anemia and glomerulosclerosis. Mutations in the LCAT gene that result in some residual LCAT activity lead to Fish Eye disease, characterized by opacity of the cornea and hypoalphalipoproteinemia. H.-G. Klein et al. (1992) *J. Clin. Invest.* 89:499–506.

Thus, there is a need for compositions and methods for the prophylactic and therapeutic treatment of atherosclerosis and conditions associated with LCAT deficiency. This invention satisfies this need by providing compositions and methods for increasing the serum level of LCAT activity.

SUMMARY OF THE INVENTION

It has been discovered that increasing the level of lecithin-cholesterol acyltransferase activity in a rabbit (which is an accepted model of the development of atherosclerosis in humans; D. J. Gordon and B. M. Rifkind (1989) *N. Engi. J. Med.* 321:1311), causes a decrease in the accumulation of cholesterol in the arteries. This discovery is surprising because no prior results had indicated that increasing the level of LCAT activity would have such an effect. In the rabbit model, increasing the mass quantity of human LCAT in the serum by about five times above the normal human level also led to significant decreases in total triglycerides, at least five-fold increases in the amount of high density lipoproteins and about a seven-fold decrease in the ratio of total cholesterol to high density lipoproteins in animals fed a high cholesterol diet. Therefore, increasing LCAT activity in the serum of humans, rabbits and other mammals with similar modes of lipoprotein metabolism is an effective treatment against atherosclerosis.

This invention provides methods for treating atherosclerosis in a mammalian subject, including humans, comprising the step of increasing the LCAT activity in the serum of the subject to a level effective to decrease the accumulation of cholesterol in the subject, whereby decreasing the accumulation of cholesterol provides a treatment for atherosclerosis.

In one aspect, the method involves administering to the subject a pharmaceutical composition comprising a pharmaceutically acceptable carrier and a pharmacologically effective amount of LCAT. In one embodiment, the composition is administered intravenously. This invention also provides pharmaceutical dosage forms comprising a pharmaceutically acceptable carrier and a pharmacologically effective amount of LCAT.

In another aspect, the method involves transfecting cells with a nucleic acid comprising a nucleotide sequence coding for expression of LCAT, whereby the transfected cells express LCAT and secrete sufficient LCAT into the serum to increase LCAT to a level effective to decrease the accumulation of cholesterol. In one embodiment, the method involves transfecting cells in vivo. In another embodiment, the method involves transfecting cells ex vivo and administering transfected cells that express and secrete LCAT to the subject in an amount sufficient to increase LCAT activity to a level effective to decrease the accumulation of cholesterol.

In another aspect, the methods involve administering a drug that up-regulates the endogenous production of LCAT in the subject.

In another aspect, the method involves increasing both the serum LCAT activity and the level of Apo A-I in the serum to an amount effective to decrease accumulation of cholesterol. The invention also provides vectors comprising a nucleic acid that comprises expression control sequences operatively linked to a sequence that codes for the expression of LCAT and expression control sequences operatively linked to a sequence that codes for the expression of an Apo A-I.

This invention also provides methods for treating an LCAT deficiency condition in a mammalian subject comprising increasing the LCAT activity in the serum of the subject to a therapeutically effective level. The condition can be Fish Eye Syndrome or Classic LCAT Deficiency Syndrome.

This invention also provides non-human mammals transgenic for LCAT having an absolute serum LCAT activity of at least 1000 nmol/ml/hr.

BRIEF DESCRIPTION OF THE DRAWINGS

FIG. 4 shows the significant ($<0.05$) bivariate Pearson correlations of post-diet variables with aortic atherosclerosis in control and transgenic rabbits. The intima/media ratio correlated well with the planimetry assessment of atherosclerosis in both the control group and the entire study.

FIG. 5 depicts the nucleotide sequence and deduced amino acid sequence of a genomic clone encoding a human LCAT (SEQ ID NO:1). FIG. 5A: Nucleotide sequence of nucleotides 1–1092, deduced amino acid sequence and exon start and start site. FIG. 5B: Nucleotide sequence of nucleotides 1093–2100, deduced amino acid sequence, and exon start and stop sites. FIG. 5C: Nucleotide sequence of nucleotides 2101–3108, deduced amino acid sequence, and exon start and stop sites. FIG. 5D: Nucleotide sequence of nucleotides 3109–4368, deduced amino acid sequence, and exon start and stop sites. FIG. 5E: Nucleotide sequence of nucleotides 4368–5292, deduced amino acid sequence, and exon start and stop sites. FIG. 5F: Nucleotide sequence of nucleotides 5293–6552, deduced amino acid sequence, and exon start and stop sites. FIG. 5G: Nucleotide sequence of nucleotides 6553–6901 FIG. 5F: Nucleotide sequence of nucleotides 5293–6552, deduced amino acid sequence, and exon start and stop sites.

DETAILED DESCRIPTION OF THE INVENTION

Figure 1A:
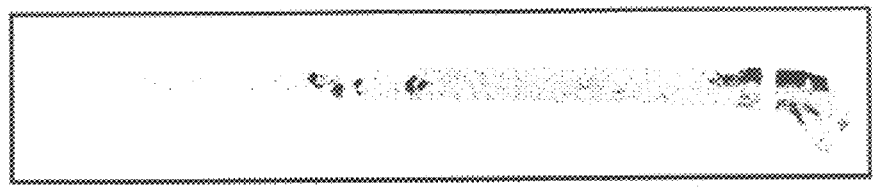
FIG. 1 depicts a comparison of the atherosclerosis in control and transgenic rabbits over-expressing human LCAT by quantitative planimetry. The aortas of LCAT transgenic and control male rabbits, fed a 0.3% cholesterol-chow diet for 17 weeks, were harvested and stained with Sudan IV. The percent of the surface area that stained was determined by planimetry of the digitized image. J. F. Cornhill et al., (1985) *Arteriosclerosis*, 5:415. Top panel: Planimetry of aortas of transgenic rabbits (n=12). Middle panel: Planimetry of aortas of control rabbits (n=10). The compilations of the images from the study groups are summarized for transgenic and control rabbits. Bottom panel: Graded shades of the probability of distribution.

Since the process of accumulating cholesterol in the arteries leads to atherosclerosis and its clinical sequelae, for example, ischemic heart disease and heart attack, stroke and peripheral vascular disease, slowing or reversing the process of cholesterol accumulation is effective in the prevention or treatment of atherosclerosis. Thus, this invention provides compositions and methods for decreasing (i.e., slowing or reversing) the accumulation of cholesterol in the arteries of a mammalian subject by increasing the level of lecithin-cholesterol acyltransferase ("LCAT") activity in the serum of the subject. In another aspect, this invention provides methods of maintaining a ratio of total serum cholesterol to serum high density lipoproteins in a mammal at below five:one, considered to be a profile of average risk for heart disease. (W. P. Castelli et al. (1986) JAMA 256:2835.) In another aspect, this invention provides methods for prophylactically or therapeutically treating atherosclerosis in a mammalian subject, in particular, a human subject, by increasing the activity of LCAT in the serum of the subject to a rate effective to decrease the accumulation of cholesterol of the subject, in particular in the arteries of the subject. In another embodiment, this invention provides methods for treating conditions involving LCAT deficiencies, such as Fish Eye Syndrome and Classic LCAT Deficiency Disease. The methods involve increasing the LCAT activity in the serum to a level sufficient to ameliorate the condition and, preferably, increasing it to at least normal levels.

As used herein, "lecithin-cholesterol acyltransferase," or "LCAT," refers to a glycoprotein enzyme that can be found naturally in the blood serum of mammals, including humans, that catalyzes the synthesis of cholesterol esters and lyso-lecithin from phosphatidylcholine and unesterified cholesterol present in plasma lipoproteins. The enzyme is naturally produced primarily by the liver. Genomic DNA encoding a human LCAT of 416 amino acids has been isolated. Its nucleotide sequence and deduced amino acid sequence are provided in FIG. 5 (SEQ ID NO:1). The nucleotide and deduced amino acid sequence of an LCAT from mouse is described in C. H. Warden et al. (1989) *J. Biol. Chem.* 264:21573–81. Any mammalian LCAT or enzymatically active allelic variation of it is useful in the methods of this invention, as are other variants, including fragments of the enzyme that possess the enzymatic activity described above. An "allelic variation" in the context of a polynucleotide or a gene is an alternative form (allele) of a gene that exists in more than one form in the population. At the polypeptide level, "allelic variants" generally differ from one another by only one, or at most, a few amino acid substitutions. A "species variation" of a polynucleotide or a polypeptide is one in which the variation is naturally occurring among different species of an organism. A polypeptide "fragment" or "segment" is a stretch of amino acid residues of at least about 6 contiguous amino acids from a particular sequence, more typically at least about 12 ammo acids.

The amount of LCAT or LCAT activity in the serum can be determined in various ways. The mass of LCAT can be determined by a competitive double antibody radioimmunoassay. Routine methods also are known for measuring absolute LCAT activity in the serum and for measuring the more informative cholesterol esterification rate. See, e.g., J. J. Albers et al. *Methods in Enzymol.* 129:763–783 (1986) and M. P. T. Gillett and J. S. Owens, Chapter 7b, pp. 187–201, in *Lipoprotein Analysis—A Practical Approach*, C. A. Converse and E. R. Skinner, eds. LCAT activity can be determined by measuring the conversion of radiolabeled cholesterol to cholesteryl ester after incubation of the enzyme and radiolabeled lecithin-cholesterol liposome substrates containing Apo A-I. Endogenous cholesterol esterification rate can be determined by measuring the rate of conversion of labeled cholesterol to cholesteryl ester after incubation of fresh plasma that is labeled with a trace amount of radioactive cholesterol by equilibration with a a [$^{14}$C] cholesterol-albumin mixture at 4° C. A more detailed protocol is provided in the Examples. The endogenous cholesterol esterification rate is a better measure of the therapeutic LCAT activity because it reflects not only the amount of LCAT activity present in the serum, but also the nature and amount of substrate and cofactors in the plasma. Thus, the cholesterol esterification rate is not necessarily proportional to either mass of LCAT or absolute LCAT activity.

As used herein, "mammalian subject" refers to an individual of any mammalian species that develops signs of atherosclerosis, including humans. These signs or indicators include, for example, the development of cholesterol plaques in the arteries and calcification, the extent of which can be determined by Sudan IV staining, or the development of foam cells in an artery. Atherosclerosis also is characterized by a narrowing of the arteries detected by, for example, coronary angioplasty, ultrasound and ultrafast CT. Preferred mammalian subjects for LCAT treatment of atherosclerosis include those whose mode of lipoprotein metabolism is similar to humans and rabbits, such as non-human primates.

Prophylactic and Therapeutic Treatments

As used herein the term "treatment" refers to both prophylactic and therapeutic treatment. For example, prophylactic treatment can be administered to those subjects at risk for developing atherosclerosis. One risk factor is an atherogenic lipoprotein profile. For example, a ratio of serum cholesterol to high density lipoproteins of above 5:1 indicates a higher than average risk of developing atherosclerosis. Other factors indicating increased risk for atherosclerosis include a serum cholesterol level of above about 240 mg/dl; a high density lipoprotein level below about 35 mg/dl; and a low density lipoprotein level above about 190 mg/dl. Therapeutically, the treatment of this invention can be administered to individuals already suffering from atherosclerosis or a disease associated with it.

The level of serum LCAT activity effective to decrease accumulation of cholesterol depends on several factors, including the species, the manner of administration, the general health of the subject, the desired result (e.g., prophylaxis or therapeutic treatment) and the judgment of the prescribing physician. For example, the practitioner may decide what risk levels for heart disease indicate prophylactic treatment, and what target level of LCAT is indicated for the treatment of a person already suffering from atherosclerosis. LCAT levels sufficient to measurably decrease the rate of accumulation of cholesterol are at least about one-and-a-half times the normal cholesterol esterification rate for the mammalian species and, more preferably, at least about two times, at least about five times, at least about ten times, at least about fifteen times or at least about twenty times.

In humans, the normal cholesterol esterification rate ranges from about 60 nmol/ml/hr to about 130 nmol/ml/hr. The effective treatment of atherosclerosis in humans can involve increasing the level of serum LCAT activity to achieve a cholesterol esterification rate of at least 200 nmol/ml/hr, at least 250 nmol/ml/hr, at least 500 nmol/ml/hr, at least 1000 nmol/ml/hr or at least 2000 nmol/ml/hr. Increasing the mass of LCAT in the serum results in an increase in cholesterol esterification rates. Normally, humans have about 5 µg LCAT per ml serum. Thus, increasing LCAT to at least 10 µg/ml of serum can increase the cholesterol esterification rate to anti-atherosclerotic levels. Increasing LCAT to at least 15 µg/ml of serum, at least 25 µg/ml of serum, at least 50 µg/ml of serum or at least 100 µg/ml of serum also can achieve these ends.

Methods for Increasing Serum Levels of LCAT

The serum level of LCAT can be increased by any means available. This includes, without limitation, direct administration of the LCAT enzyme, expression of LCAT through gene therapy and the up-regulation of endogenous LCAT through the administration of drugs.

1. Administration of LCAT Enzyme

The level of LCAT activity in a subject can be increased by administering to the subject a pharmaceutical composition comprising a pharmaceutically acceptable carrier and a pharmacologically effective amount LCAT. A pharmacologically effective amount of LCAT is an amount effective to decrease the rate of accumulation of cholesterol in a subject. As used herein, the term "pharmaceutical composition" refers to a composition suitable for pharmaceutical use in a mammal. Thus, pharmaceutical compositions are relatively non-toxic to the animal to whom the composition is administered.

"Pharmaceutically acceptable carrier" encompasses any of the standard pharmaceutical carriers, buffers and excipients, such as a phosphate buffered saline solution, water, and emulsions. Suitable pharmaceutical carriers and their formulations are described in Martin, *Remington's Pharmaceutical Sciences*, 19th Ed. (Mack Publishing Co., Easton 1995). Liquids are the preferred pharmaceutical carriers for the preparation of the pharmaceutical compositions of this invention.

The pharmaceutical compositions are intended for all well known forms of administration and, in particular, parenteral administration for prophylactic and/or therapeutic treatment. Local administration, such as transdermally, also is contemplated. The pharmaceutical compositions can be administered in a variety of unit dosage forms depending upon the method of administration. For example, unit dosage forms for parenteral administration include unit doses of injectable solutions.

LCAT can be administered by any means known in the art for delivery of proteins. However, systemic administration by injection is preferred. This includes intramuscular, intravenous, intraperitoneal, and subcutaneous injection. Injection can be automated by, for example, a programmable pump. Thus, this invention provides compositions for intravenous administration which comprise a solution of LCAT dissolved or suspended in an acceptable carrier, preferably an aqueous carrier. A variety of aqueous carriers can be used, e.g., water, buffered water, 0.4% saline, and the like. For instance, phosphate buffered saline (PBS) is particularly suitable for administration of LCAT protein. These compositions can be sterilized by conventional, well-known sterilization techniques, or can be sterile filtered. Additives can also include additional active ingredients such as bactericidal agents, or stabilizers. The resulting aqueous solutions can be packaged for use as is, or lyophilized, the lyophilized preparation being combined with a sterile aqueous solution prior to administration. The compositions can contain pharmaceutically acceptable auxiliary substances as required to approximate physiological conditions, such as pH-adjusting and buffering agents, tonicity-adjusting agents, wetting agents and the like, for example, sodium acetate, sodium lactate, sodium chloride, potassium chloride, calcium chloride, sorbitan monolaurate, triethanolamine oleate, etc.

LCAT also can be systemically administered transmucosally or transdermally. For transmucosal or transdermal administration, penetrants appropriate to the barrier to be permeated are used in the formulation. Such penetrations are generally known in the art, and include, for example, for transmucosal administration, bile salts and fusidic acid derivatives. In addition, detergents can be used to facilitate permeation. Transmucosal administration can be through nasal sprays, for example, or using suppositories.

The form, amounts and timing of administration generally are a matter for determination by the practitioner. In one embodiment, the pharmaceutical composition is delivered as a unit dosage form. It is estimated that about 40 mg LCAT suffices to increase the amount of serum LCAT in a human about two-fold. Accordingly, a unit dosage form can contain about 10 mg to about 1000 mg or about 40 mg to about 200 mg. In certain embodiments, the dosage form has about 100 mg, or about 500 mg LCAT. Depending on the target level of LCAT to be maintained and timing of delivery, small doses can be administered frequently, or large doses can be administered less frequently.

The invention contemplates several sources of LCAT for incorporation into pharmaceutical compositions. LCAT can be isolated from plasma. A method for isolating LCAT from human serum is described in the Examples.

Alternatively, LCAT can be recombinant LCAT and, more particularly, recombinant human LCAT. J. McLean et al. (1986) *Proc. Nat'l. Acad. Sci. USA* 83:2335–2339 describes the cloning and sequence of a human LCAT cDNA. J. McLean et al. (1986) *Nucl. Acids Res.* 14:9397–9406 describes a complete gene sequence for human LCAT. (See FIG. 5.) J. S. Hill et al. (1993) *J. Lipid Res.*, 34:1245–1251 describes the expression of recombinant LCAT. Methods of preparing expression vectors are described in further detail below. These vectors can be used to express recombinant LCAT in a variety of expression systems including mammalian, insect and bacterial systems. The unicellular hosts may be prokaryotic or eukaryotic and include, for example, *E. coli*, yeast, insect cells, COS cells or Chinese Hamster Ovary ("CHO") cells. A method for expressing LCAT in COS-7 cells is described in J. McLean (1986) *Proc. Nat'L Acad. Sci., USA.*, 83:2335–2339. Expression control sequences can be chosen as appropriate. Recombinant LCAT can then be purified by e.g., the method described in the Examples.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide. The construction of expression vectors and the expression of genes in transfected cells involves the use of molecular cloning techniques also well known in the art. Sambrook et al., *Molecular Cloning—A Laboratory Manual*, Cold Spring Harbor Laboratory, Cold Spring Harbor, N.Y., (1989) and *Current Protocols in Molecular Biology*, F. M. Ausubel et al., eds., (Current Protocols, a joint venture between Greene Publishing Associates, Inc. and John Wiley & Sons, Inc.

2. Gene Therapy

In one aspect, the level of LCAT activity is increased through the use of gene therapy. As used herein, "gene therapy" refers to the transfer and, preferably, stable integration of new genetic information into cells in a subject. Methods of increasing LCAT activity levels by gene therapy involve transfecting cells with a nucleic acid that includes a nucleic acid sequence coding for expression of LCAT. The transfected cells express LCAT and secrete it into the serum of the subject. The cells are transfected in sufficient number or for such high expression of LCAT that they increase the amount of LCAT to a level effective to decrease the accumulation of cholesterol. Genes encoding LCAT are introduced into the subject in one of two ways. In one embodiment, the genes are introduced into cells of the individual in vivo by means of expression vectors. In another embodiment, the genes are introduced into cells ex vivo, and transfected cells that express and secrete LCAT are administered to the subject.

In in vivo approaches, liver cells are useful targets for transfection. Liver cells produce LCAT, so they possess the processing machinery for making the enzyme recombinantly. Furthermore, vectors injected into the blood stream quickly pass through the liver, so liver cells are quickly exposed to the vectors. Hematopoietic stem cells also are useful targets for gene therapy because they multiply rapidly, thereby creating more cells capable of producing LCAT. vivo approaches also are attractive because they allow more control over the transfection process. For example, transfected cells can be tested and the ones which express LCAT in the highest amounts can be selected. Hematopoietic stem cells can be taken from the subject, transfected ex vivo and reintroduced into the subject. Therefore, in one embodiment, the cells are cells from the subject. While allografts can be useful, syngeneic grafts are most useful since they are least likely to elicit a host-vs-graft response.

Methods of transfecting genes into mammalian cells, either in vivo and ex vivo, and obtaining their expression are well known to the art. These include, for example, transfecting cells with the nucleic acid by means of nucleic acid vectors, such as viral vectors (including, e.g., retroviral vectors, adenoviral vectors, adeno-associated viral vectors, hepatitis viral vectors, vaccinia viral vectors and herpes viral vectors), plasmid vectors, cosmid vectors, microencapsulation vectors (e.g., cationic or uncharged liposomal microspheres); microinjection; electroporation; chromosome transfer; calcium precipitation; or biolistic injection (e.g., attaching DNA to a particle, such as a gold bead, and propelling it into a cell). See also, e.g., *Methods in Enzymology*, vol. 185, Academic Press, Inc., San Diego, Calif. (D. V. Goeddel, ed.) (1990) or M. Kriegler, *Gene Transfer and Expression—A Laboratory Manual*, Stockton Press, New York, N.Y., (1990).

Viral vectors are particularly useful for gene therapy. Methods for constructing and using viral vectors are known in the art and are reviewed, for example, in Miller and Rosman (1992) *Biotechniques*, 7:980–990. The targeting specificity of viral vectors can be utilized to target predetermined cell types and introduce a nucleic acid molecule into the cell. Thus, the viral vector selected will depend, in part, on the cell type to be targeted. For example, hepatocytes, which normally produce LCAT, are an attractive target for transfection. In addition, a viral vector can be made tissue-specific by incorporating a tissue-specific promoter or enhancer into the vector.

Adenoviruses are useful vectors for the transfer of genes into cells. Liver cells have an adenovirus receptor. Therefore, upon intravenous injection of a recombinant adenovirus, about 95% of the viruses will selectively infect liver cells. Replication-defective adenoviral vectors can be prepared by deletion of sequences spanning E1A, E1B, and a portion of the E3 region, impairing the ability of this virus to replicate or transform non-permissive cells. See, e.g., Hurwitz et al. (1985) *Proc. Natl. Acad. Sci. U.S.A.* 82:163–167. The early enhancer/promoter of the cytomegalovirus can be used to drive transcription of an inserted LCAT gene with an SV40 polyadenylation sequence cloned downstream from this reporter. High titer recombinant adenovirus can be prepared by amplification in LE293 cells using established methods. Virus can be purified from cell lysates by cesium chloride gradient ultra-centrifugation followed by de-salting on Sephadex G-50 (Sigma Biochemicals, St. Louis Mo.) column in PBS. Purified virus then can be used for injection into the subject. Adenoviral vectors in which the E4 region has been deleted also are attractive as second-generation adenoviral vectors that have prolonged expression and less possible immunogenicity.

Adenoassociated virus (AAV), is a single-stranded, DNA parvovirus. AAV vectors have several advantages which make them desirable as gene delivery systems. They have no known mode of pathogenesis and 80% of people in the United States are currently seropositive for AAV. Ostrove et al. (1981) *Virology* 113:521; Cukor et al., in *The Parvoviruses* (ed. Berns, Plenum, N.Y., 1984). AAV virions are resistant to physical treatments, such as sonication and heat inactivation not tolerated by other viruses during purification. Samulski et al. (1989) *J. Virol.* 63:3822–3828. Unlike retroviruses, infection and/or transduction of non-dividing cells is possible. Like retroviruses, AAV integrates into the host cell genome upon infection. Kotin et al. (1990) *Proc. Natl. Acad. Sci. USA* 87:2211–2215; Samulski et al. (1991) *EMBO J.* 10:3941–3950. However, unlike retroviruses, AAV preferentially integrates at a specific chromosomal site (19q13.3). At this site, AAV does not cause any significant alteration in the growth properties or morphological characteristics of human cells. Furthermore, integration of AAV into the cellular genome can occur in non-proliferating cells. Lebkowski et al. (1988) *Mol. Cell. Biol.* 8:3988–3996. AAV also possess a reasonably large cloning capacity, slightly more than half that of retroviral vectors. Recombinant AAV vectors contain no endogenous promoter activity, allowing for specific promoter choices to be made depending on target cell type, without regard for complications arising from endogenous viral promoters. Unlike retroviral vectors, packaged AAV vectors can be concentrated so that multiplicities of infection exceeding 1.0 can be used in transduction experiments. This means that virtually 100% of the targets in a culture could be transduced, obviating the need for a selection step.

AAV is a defective virus that grows only in cells in which certain functions are provided by a co-infecting helper virus such as adenoviruses and herpesviruses. Infection of cells with AAV in the absence of helper functions results in integration of AAV into the host cell genome without replication. The AAV genome has two copies of a 145-nucleotide-long ITR (inverted terminal repeat), one at each end. Srivastava et al. (1983) *J. Virol.* 45:555–564. The ITR sequences provide an origin of replication and also mediate integration and excision of the AAV genome from the cell genome.

The sequence between the ITRs of about 4470 nucleotides contains two open reading frames for rep and cap genes. Hermonat et al. (1984) *Virology* 51:329–339. The cap gene encodes capsid proteins. The rep genne encodes proteins known to be required for replication. Rep$^-$ vectors may show reduced preference for site-specific integration into chromosome 19. However, the overall integration frequency of rep$^-$ vectors is about 80-fold higher integration frequency than comparable rep$^+$ vectors, suggesting rep inhibits rather than facilitates integration. McLaughlin et al. (1988) *J. Vitrol.* 62:1963–1973.

In recombinant AAV, all protein coding sequences (such as cap, lip and rep) can be replaced by the LCAT encoding sequence. Recombinant AAV is replicated by co-transfecting a cell bearing the AAV vector carrying the gene of interest, together with a helper AAV plasmid that expresses all of the essential AAV genes, into adenovirus- or herpes-infected cells, which supply additional helper functions necessary for AAV replication and the production of new viral particles.

A further method has been proposed in which a recombinant vector containing AAV ITR sequences but lacking all other AAV sequences is surrounded by cationic lipids and introduced into a cell by lipofection. Phillip et al., WO 95/07995.

In the case of non-infectious viral vectors, the helper virus genome is usually mutated to destroy the viral packaging signal required to encapsulate the nucleic acid into viral particles. However, the helper virus retains structural genes required to package a co-introduced recombinant virus containing a gene of interest. Without a packaging signal, viral particles will not contain a genome and, thus, cannot proceed through subsequent rounds of infection.

Retroviral vectors can be used for in vivo or ex vivo targeting and therapy procedures. Retroviral vectors can be constructed either to function as infectious particles or to undergo only a single initial round of infection. In the former case, the genome of the virus is modified so that it maintains the necessary genes, regulatory sequences and packaging signals to synthesize new viral proteins and RNA. However, genes conferring oncogenic potential of these viruses are destroyed. After the viral proteins are synthesized, the host cell packages the RNA into new viral particles, which can undergo further rounds of infection. The viral genome also is engineered to encode and express the desired recombinant protein. Improved methods of transfection of peripheral blood lymphocytes by retroviral vectors are described in Yang et al. (1995) *Nature Medicine* 1(9):890–893 and Bunnell et al. (1995) *Proc. Acad. Nat'l Sci. USA* 92:7739–7743.

A retroviral packaging cell line such, as PA317 (American Type Culture Collection, Bethesda, Md., accession number CRL 9078) can be used to create infective amphotrophic retroviral vectors. The retroviral plasmid, pLNCX (D. Miller and G. Rosman (1989) *Biotechniques* 7:980) can contain the expression control sequence operatively linked to the nucleic acid sequence to be expressed at "X". That plasmid contains a Maloney murine leukemia virus LTR promoter/enhancer (L); neomycin resistance gene encoding neomycin phosphotransferase (N); a human cytomegalic virus LTR/enhancer (C) and the coding gene to be expressed (X). The LCAT gene is inserted by standard techniques at a pre-existing cloning site by replacement of the phosphotransferase gene for neomycin resistance for one encoding a phosphotransferase of hygromycin resistance.

Retroviruses have been the preferred vehicle for gene delivery into human hematopoietic stem cells because of their high efficiency of gene transfer and the co-linear and stable integration of the transferred genes into chromosomal DNA. However, genes from retroviruses can integrate into the host cell chromosome only if the cell is actively dividing.

Nucleic acids used to transfect cells with the LCAT gene generally will be in the form of an expression vector including an expression control sequence operatively linked to a nucleotide sequence coding for expression of LCAT. The term "expression control sequence" refers to a nucleotide sequence in a polynucleotide that regulates the expression (transcription and/or translation) of a nucleotide sequence operatively linked thereto. The term "operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

Appropriate expression control sequences for mammalian cells include, for example, the SV40 promoter, the RSV (Rous sarcoma virus) promoter, the CMV (cytomegalovirus) promoter and the metallothionein promoter. The CMV promoter is preferred for transient expression systems. The metallothionein promoter is preferred for stable expression systems. Promoters can be constitutive or can be tissue-specific for the target cell type, e.g., specific for hepatocytes. Expression control sequences providing high levels of expression are preferable for producing LCAT in quantities sufficient to cause a decrease in the accumulation of cholesterol.

As used, the term "coding for expression of LCAT" refers to sequences that, upon transcription and translation of mRNA, produce polypeptide sequences of the LCAT enzyme. Thus, for example, cDNA, genomic DNA with introns removed upon transcription and processing into MRNA, and degenerate sequences encoding LCAT, all code for expression of LCAT. DNA sequences coding for expression of LCAT can be obtained by any methods known in the art. For example, coding sequences can be prepared by chemical synthesis. Also, PCR primers can be devised using the sequences of LCAT provided herein and cDNA or genomic DNA can be isolated by amplification. The following polynucleotides are useful as primers to create probes for isolating from a library a cDNA or genomic clone encoding a human LCAT.

1. Probe I: a 340 bp 5' LCAT exon 1 probe
    Sense oligo: 5' GGC TCC CTG AGG CTG TGC CCC TTT 3'
    (SEQ ID NO:2)
    Antisense oligo: 5' TGG CGT GGT GCA TCA GGG GCC TGG 3'
    (SEQ ID NO:3)
2. Probe II: a 380 bp 3' LCAT probe
    Sense oligo: 5° CTG GTG TGG AAG TAT ACT GCT TTT 3'
    (SEQ ID NO:4)
    Antisense oligo: 5° CTT CAA CCT GAA ACA TAG CCA TCA 3'
    (SEQ ID NO:5)

The technique of "polymerase chain reaction," or "PCR," as used herein generally refers to a procedure wherein minute amounts of a specific piece of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands on the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See, generally, Mullis et al. (1987) *Cold Spring Harbor Symp. Quant. Biol.* 51:263; Erlich, ed., PCR *Technology*, (Stockton Press, N.Y., 1989). As used herein, PCR is considered to be one, but not the only, example of a nucleic acid polymerase reaction method for amplifying a nucleic acid test sample, comprising the use of a known nucleic acid (DNA or RNA) as a primer.

An "isolated polynucleotide" is a polynucleotide, e.g., an RNA, DNA, or a mixed polymer, which is substantially separated from other DNA sequences which naturally accompany a native human sequence, e.g., ribosomes, polymerases, and many other human genome sequences. The term embraces a polynucleotide sequence which has been removed from its naturally occurring environment, and includes recombinant or cloned DNA isolates and chemically synthesized analogues or analogues biologically synthesized by heterologous systems. A substantially pure molecule includes isolated forms of the molecule. An "isolated polypeptide" or protein carries a similar meaning with the polypeptide or protein being substantially separated from any cellular contaminants and components naturally associated with the protein in vivo, so that it is the predominant macromolecular species in the composition.

Some of the disadvantages stemming from the use of viral vectors are avoided by transfecting a DNA fragment into cells nonbiologically, for example, by lipofection, chemical transformation, electroporation or biolistic injection. In these approaches, ample amounts of pure DNA can be prepared for transfections, and much larger fragments can be accommodated. Such approaches are preferred for cells that can be temporarily removed from the body.

The term "recombinant" or "recombinant DNA molecule" refers to a nucleic acid sequence which is not naturally occurring, or is made by the artificial combination of two otherwise separated segments of sequence. By "recombinantly produced" is meant artificial combination often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the common natural forms. Restriction enzyme recognition sites are often the target of such artificial manipulations, but other site specific targets, e.g., promoters, DNA replication sites, regulation sequences, control sequences, or other useful features may be incorporated by design. "Recombinant DNA molecules" include cloning and expression vectors. A "fragment" of a polynucleotide is a stretch of at least about 18 nucleotides, more typically at least about 40 nucleotides.

3. Up-Regulation of Endogenous LCAT

Another method for increasing the serum level of LCAT activity is through the administration of drugs that up-regulate the endogenous production of LCAT in the subject. Androgens already are known to down-regulate the expression of LCAT. J. J. Albers et al. *Biochim. Biophys. Acta* 795:293–296 (1984). Also, LCAT levels are higher in females than in males. J. J. Albers et al. *Atherosclerosis* 43:369–379 (1983). It is expected that estrogens and estrogen analogs up-regulate expression of LCAT. The amounts of such drugs to be administered can be determined empirically by the practitioner.

Candidate drugs can be identified by screening compounds for the ability to increase LCAT expression in animal models or in in vitro models. In animal models, the candidate drug can be administered to an animal to determine the effect on LCAT activity in the animal. Alternatively, after administration, the animal can be examined to determine the effect of the drug on the development of atherosclerosis.

Candidate drugs can be identified by screening compounds for the ability to increase LCAT activity in vitro. In one method, the compound is tested for its effect on the ability of LCAT to cause esterification of cholesterol to cholesteryl ester in an LCAT activity assay such as that described above.

Further Methods of Treatment

The metabolism of cholesterol involves both the loading of cholesterol onto HDL particles through esterification by LCAT and the transport of cholesterol to the liver by HDL. It is known that increasing Apo A-I decreases the risk of heart disease. A. C. Liu et al. (1994) *J. Lipid Res.* 35:2263–2267 and C. Paszty et al. (1994) *J. Clin. Invest.* 94:899–903. Certain versions of Apo A-I, such as Apo A-I milano, are particularly protective. C. R. Sirtori et al. (1995) *Atherosclerosis* X pp. 50–55, Elsevier Science, NY and S. Ameli et al. (1994) *Circulation* 90:1935–41. Furthermore, Apo A-I is a cofactor of LCAT activity. C. J. Fielding et al. (1972) *Biochim Biophys. Acta* 270:513–518. Accordingly, increasing the activity of LCAT in the serum of the subject combined with increasing the transport of cholesterol to the liver by increasing serum HDL or by providing HDL with better cholesterol loading characteristics produces a synergistic effect for decreasing the accumulation of cholesterol in the arteries of a subject. In one embodiment, the invention involves increasing both LCAT and the level of Apo A-I in the serum of a subject to an amount effective to decrease accumulation of cholesterol. The amount of Apo A-I in the serum of a human normally is about 130 mg/dl. In the methods of this invention, levels of Apo A-I can be increased to at least 150 mg/dl or at least 300 mg/dl. In one embodiment, the levels of both Apo A-I and Apo A-I milano are increased. Apo A-I milano also is increased to at least 150 mg/dl or at least 300 mg/dl. Methods for increasing the amount of Apo A-I include any of already described for increasing the levels of LCAT. Methods of producing Apo A-I are described in U.S. Pat. No. 4,943,527 (Protter et al.).

This invention also provides expression vectors comprising a nucleic acid that includes expression control sequences operatively linked to a sequence that codes for the expression of LCAT. In another embodiment this invention provides expression vectors comprising a nucleic acid that includes expression control sequences operatively linked to a sequence that codes for the expression of LCAT and expression control sequences operatively linked to a sequence that codes for the expression of an Apo A-I protein, including, e.g., Apo A-I milano.

Treatment of Conditions Related to LCAT Deficiency

In another aspect, this invention provides methods for treating conditions stemming from a deficiency of LCAT activity, such as Classic LCAT Deficiency Syndrome, in which LCAT is absent, and Fish Eye Syndrome, in which the individual has only partial, residual LCAT activity levels. The methods involve increasing serum LCAT activity levels in such individuals to a therapeutically effective level. Increasing LCAT serum levels to about normal levels, i.e., to achieve a cholesterol esterification rate at least 60 nmol/ml/hr or at least 130 mnol/ml/hr, are therapeutically effective. Also, LCAT can be increased to achieve a cholesterol esterification rate above normal levels, e.g., rates of about 200 nmol/ml/hr, 300 nmol/mI/hr, 500 nmoUml/hr or 1000 nmol/ml/hr. Increasing the mass of LCAT in the serum to about 5 µg/ml, or higher, e.g., about 10 µg/ml, about 20 µg/ml, about 50 µg/ml or about 100 µg/ml, also achieves these results. LCAT levels can be increased by any of the methods described above.

Transgenic Non-Human Mammals

This invention also provides non-human mammals transgenic for LCAT whose serum has a cholesterol esterification rate of at least 1.5 times or at least two times the normal level, or an absolute LCAT serum activity of at least 1000 nmol/ml/hr and, preferably, at least 1500 nmol/ml/hr. These animals are useful in the production of healthier livestock, in the study of atherosclerosis and as screens for compounds that increase or decrease the accumulation of cholesterol. As used herein, "mammal transgenic for LCAT" refers to a mammal whose germ cells (i.e., oocytes or sperm), at least, comprise a recombinant nucleic acid molecule comprising expression control sequences operatively linked to a nucleic acid sequence coding for expression of LCAT. In one embodiment, the expression control sequences are not naturally found operatively linked to LCAT. In a preferred embodiment, the recombinant nucleic acid comprises a non-native LCAT coding sequence, i.e., an LCAT sequence that the species does not produce in nature. In one embodiment, the LCAT is a human LCAT. Particularly useful transgenic mammals of this invention include rabbits and rodents such as mice. Transgenic non-human mammals of this invention can be produced as described in the Examples.

EXAMPLES

Determination of Endogenous Cholesterol Esterification Rate

J. J. Albers et al. (1986) *Methods in Enzymology* 129:763–783 describe the following method for determining endogenous cholesterol esterification rate. For every 25 assays, the enzymatic color reagent is made fresh daily by mixing 0.1 ml of 1 mg cholesterol oxidase/ml solution. 1 ml of 2 mg peroxidase/ml solution, 1 ml of 20 mg 4-aminoantipyrine/ml solution, 1 ml of 50 mg 2.4-dibromophenol/ml solution, 3.75 ml of 2% sodium cholate solution, and 30.65 ml of assay buffer. Forty microliters of fresh plasma is pipetted into glass tubes, in septuplicate for both control and test samples. At zero time, 20 µl of 150 mM iodoacetate solution is added to each control sample to inhibit the LCAT reaction, whereas 20 µl of incubation buffer (50 mM phosphate buffer, pH 7.4) is added to each test sample. All samples are incubated at 37° for 40 min. At the end of this incubation, 20 µl of 150 mM iodoacetate solution is added to each test sample and 20 µl of incubation buffer is added to each control sample. Then, 1.5 ml each of color reagent is added to all samples and the mixtures are incubated for 10 min at 37°. The absorbance of the assay mixtures are incubated for 10 min at 37°. The absorbance of the assay mixtures is measured spectrophotometrically at a wavelength of 500 nm. Unesterified cholesterol in each sample is determined by comparison against the color of cholesterol standard solution containing 1 to 100 µg of unesterified cholesterol in which color is developed in the same manner in the sample solution. The rate of cholesterol esterification is obtained by subtraction of the amount of cholesterol in the test samples from that in the control samples. The rate can be expressed as both fractional cholesterol esterification rate (percentage decrease in unesterified cholesterol/hr) and molar cholesterol esterification rate (nmol decrease in unesterified cholesterol/ml plasma/hr).

Isolation of LCAT

J. J. Albers et al. *Methods in Enzymol.*, 129:763–783 (1986) describes the following method for isolating LCAT. Plasma is precipitated with dextran sulfate-$Mg^{2+}$ (500 mM $MgCl_2$) and the plasma is collected. The mixture is added to a Phenyl-Sepharose chromatography column and equilibrated to 10 mM Tris, 140 mM NaCl, and 1 mM EDTA, pH 7.4. LCAT is eluted by washing the column with distilled water. LCAT-containing fractions are dialyzed against 20 mM sodium phosphate, pH 7.1, and passed through an Affi-Gel Blue column with this buffer. LCAT-containing fractions are isolated. These fractions are equilibrated to 1 mM Tris, 5 mM EDTA and 25 mM NaCl, pH 7.4. The mixture is subjected to DEAE-Sepharose chromatography and LCAT is eluted with a linear NaCl-Tris gradient (25 mM NaCl, 1 mM Tris to 200 mM NaCl, 10 mM Tris) containing 5 mM EDTA. LCAT-containing fractions are then subject to hydroxylapatite chromatography. LCAT is eluted with a linear phosphate gradient (15 mM to 60 mM), pH 6.9, 150 mM NaCl. The LCAT-containing fractions are subject to Sephacryl S-200 gel filtration and eluted with 10 mM Tris, 140 mM NaCl, 1 mM EDTA, pH 7.4.

Producing Transgenic Animals

Methods for producing transgenic mammals are described in, e.g., C. P. Landel (1991) *GATA* 8:83–94. Superovulation is induced, by, e.g., first administration of pregnant mare's serum, followed by administration of exogenous gonadotrophin forty-two to forty-eight hours later. Then the animals are allowed to mate. Fertilized eggs for microinjection are then collected from superovulated donor females. The females are sacrificed and the oviducts removed. The eggs are removed from the oviduct and washed in buffer M2, described below in Table 1. The eggs are cultured and separated from cumulus cells in buffer M16, described below. The eggs are microinjected with purified DNA fragments coding for expression of LCAT. Intact, microinjected eggs are implanted into the oviducts of foster mothers made pseudopregnant by mating with sterile males. Transgenic non-human animals are identified among the offspring born to the foster mothers.

The Effect of Increased LCAT on Atherosclerosis in Transgenic Animals

The effect of increased levels of human LCAT on atherosclerosis in the rabbit was studied. The rabbit has been the principal animal species used to study the development of atherosclerosis caused by dietary cholesterol for more than 80 years (N. Anitschkow and S. Chalatow (1913) *Zentralbl. Allg. Path. Anat.* 24:1–9). This sensitivity to dietary cholesterol leads to atherosclerosis in the rabbit resembling human atherosclerotic plaques (M. L. Overturf and D. S. Loose-Mitchell (1992) *Curr. Opin. Lipidol.* 3:179–185). Rabbit very low density lipoproteins are similar in their chemical composition, apolipoprotein content, and electrophoretic mobility with agarose gel electrophoresis to human very-low-density lipoproteins. M. J. Chapman (1980) *J. Lipid Res.* 21:789–853. In addition, apolipoprotein B, an apolipoprotein involved in atherogenesis, is evident in rabbit intermediate density lipoproteins and low density lipoproteins closely resembling that seen in man. Id. Like humans, the rabbit expresses cholesterol ester transfer protein which not only permits the transfer of high density lipoprotein-derived cholesterol ester to apolipoprotein B-containing lipoprotein particles, but also is likely to play a role in the diet-induced atherosclerosis thai rabbits develop (A. R. Tall (1993) *J. Lipid Res.* 34:1255–1274). Therefore the rabbit model system affords an excellent means of detecting and quantifying the impact of potential therapies to treat and prevent atherosclerosis in humans.

A construct containing the full-length human genomic LCAT gene was used to generate transgenic animals. B. L. Vaisman et al. (1995) *J. Biol. Chem.* 270:12269. This construct contained all of the introns and 851 bp of the 5' and 1134 bp of the 3' untranslated regions of the human LCAT gene. A cosmid library made from human genomic white blood cell DNA was screened with a full length human LCAT cDNA probe as described. J. Sambrook et al. *Molecular Cloning: A Laboratory Manual*, Cold Spring Harbor Laboratory Press, (1989) and B. L. Vaisman et al. (1995) *J. Biol. Chem.* 270:12269–12275. DNA from identified clones was prepared by alkaline lysis miniprep DNA isolation (J. Sambrook et al., supra) and digested with the restriction enzyme Sma I (New England Biolabs, Beverly, Mass.). The 6.2 kb Sma I fragment was isolated from agarose gel by gene cleaning (Gene Clean Bio101 Inc., La Jolla, Calif.) followed by subcloning into bluescript IIKS-(Stratagene, La Jolla, Calif.) to generate a 9.16 kb plasmid. After amplification in *E. coli*, plasmid DNA was isolated by double CsCl banding (S. S. Fojo (1984) *Biochem. Biophys. Res. Commun.*, 124:308–313) followed by extensive dialysis and digestion with Sma I. The 6.2 kb fragment Sma I fragment was then re-isolated from agarose gels and gene cleaned (Gene Clean Bio101 Inc., La Jolla, Calif.). The gene cleaned fragment was repurified by CsCl banding, followed by extensive dialysis against injection buffer (10 mM tris pH 7.5, 0.1 EDTA) prior to microinjection.

The generation of transgenic rabbits was approved by the Animal Care and Use Committee of the National Heart, Lung, and Blood Institute. Transgenic animals were produced essentially as described above by transfecting with the Sma I fragment coding for expression of LCAT, above.

In studying the extent of atherosclerosis, animals were sacrificed by premedication with xylazine (3 mg/pound), ketamine (15 mg/pound), and robinul (0.25 ml/10 pounds) intramuscularly before either isoflurane inhalation anesthesia or euthanasia via intravenous sodium pentobarbital.

High level of expression of human LCAT led to elevated levels of HDL cholesterol concentrations in the rabbit. J. M. Hoeg et al. (1994) *Atherosclerosis* 109:11, abstract. This T-1 founder line was expanded for these studies. A total of 10 LCAT transgenic and 9 control males 5–6 moths of age were studied. The human LCAT mass in the transgenic plasma was 27.25±6.27 µg/ml (mean±SD), which was more than 5-fold the mean LCAT mass 5.56+/0.91 µg/ml reported in humans. J. J. Albers et al. (1982) *Atherosclerosis* 43:369. Expression of human LCAT led to LCAT activity at baseline in the transgenic rabbits was 15-fold that of controls (Table 2). Compared to controls, LCAT transgenic rabbits had a marked increase in total (617%; p<0.001) and HDL cholesterol concentrations (671%; p<0.001).

These rabbits were then fed a 0.3% cholesterol diet (Product number 4109000, Ziegler Brothers, Inc., Gardners, Pa.). The high cholesterol diet led to increases in the control rabbits of both total (19 fold) and especially non-HDL cholesterol concentrations (127 fold) (Table 2). In contrast, the plasma concentrations in the LCAT transgenic rabbits increased only 2-fold and 11-fold, respectively. The LCAT activity in the transgenic rabbits on the cholesterol diet remained more than 3-fold that of the control and led to an increase of HDL cholesterol concentrations to more than 5-fold that of control rabbits. The total cholesterol/HDL cholesterol ratio, a sensitive indicator of clinically detectable human atherosclerosis (W. Castelli and A. Leaf (1985) *Cardiology Clinics* 3:171), increased in the control group by-more than 12-fold. In contrast, LCAT transgenic rabbit total/HDL ratio rose less than 2-fold (Table 2) and remained below the ratio of 5 that provides an average risk for atherosclerosis in man. W. P. Castelli et al. (1986) JAMA 256:2835.

Figure 1B:
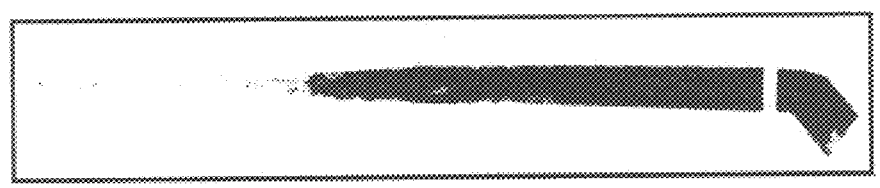

These differences in the plasma lipoprotein concentrations between control and LCAT transgenic rabbits reflected differences in the development of atherosclerosis. After 17 weeks on the 0.3% cholesterol diet, the aortae from these animals were harvested, and two methods were used to quantitate the severity of diet-induced atherosclerosis in these rabbits. Sudan IV staining of the lipid droplets permits the quantitation of the percent of the surface area developing lesions. J. F. Cornhill et al. (1985) *Arteriosclerosis* 5:415. The probability map for aortic lesion development in the transgenic rabbits (FIG. 1) shows only scattered foci of oil Sudan IV-staining material, whereas control aortae had substantial staining in the majority of the animals. The aorta of the control group had 35±7% of the surface covered by plaque. Whereas, in marked contrast, only 5±1% of the aortic surface was covered by plaque in the LCAT transgenic rabbits ($p<0.009$, FIGS. 1 and 3, right).

Figure 2:
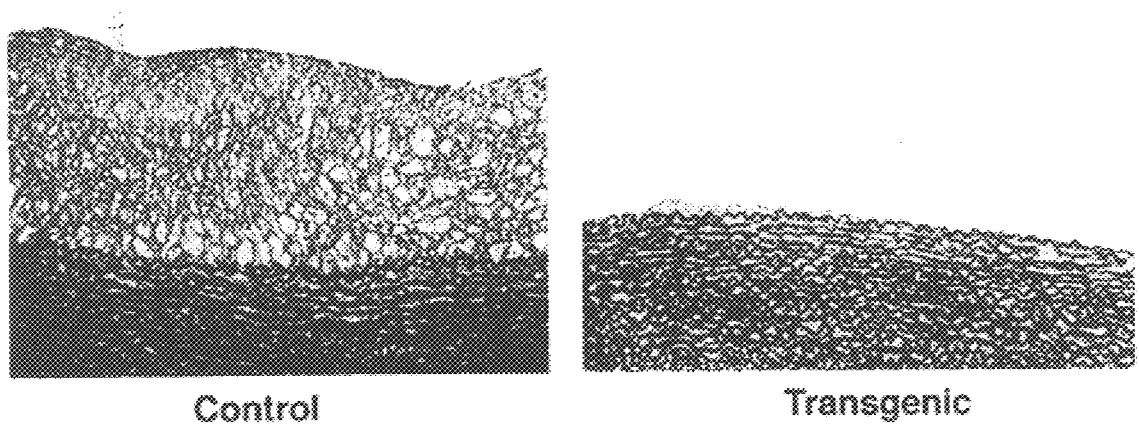
FIG. 2. Photographs of cross sections of aorta from control and transgenic rabbits fed a high cholesterol diet. A 1 mm section was taken at the descending thoracic aorta at the same position for each aorta, stained with PAS, and the degree of foam cell accumulation in the intima of the controls was compared to the lack of intimal cell formation or change in intimal cell thickness in the transgenic aortae. Left hand photograph: Cross section of aorta of control rabbit. Right hand photograph: Cross section of aorta from transgenic rabbit.
Figure 3:
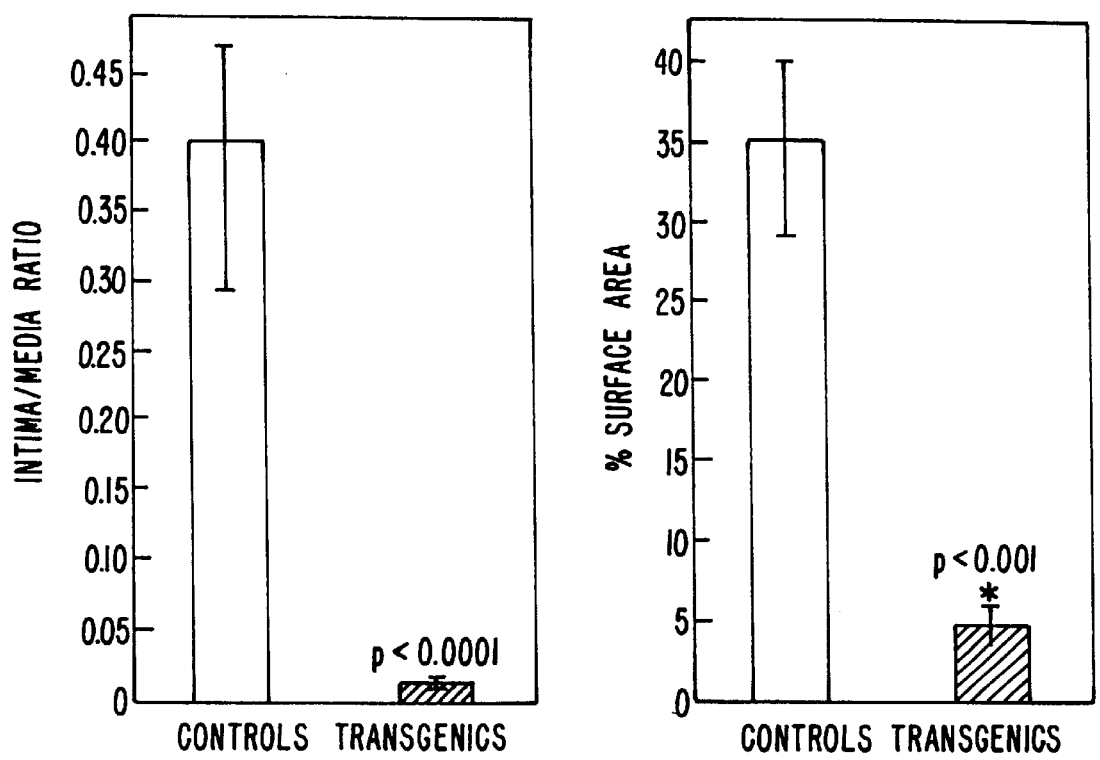
FIG. 3 shows the extent of intimal cellular proliferation as shown in FIG. 2, quantitated using a ratio of the intima to media. A. V. Chobanian et al., (1989) *Hypertension* 14:203. Left hand graph: Quantitative assessment of the intimal/media ratio ($p<0.003$). Right hand graph: Quantitative assessment of the percent of surface area ($p<0.009$). In both cases, the quantitative assessment was significantly lower in the transgenic LCAT rabbits than in controls.
Figure 4A:
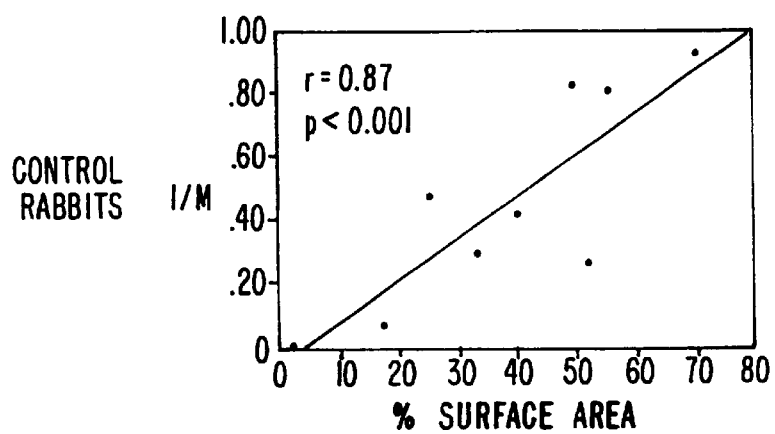
FIG. 4A: Control group, showing % surface area.
Figure 4B:
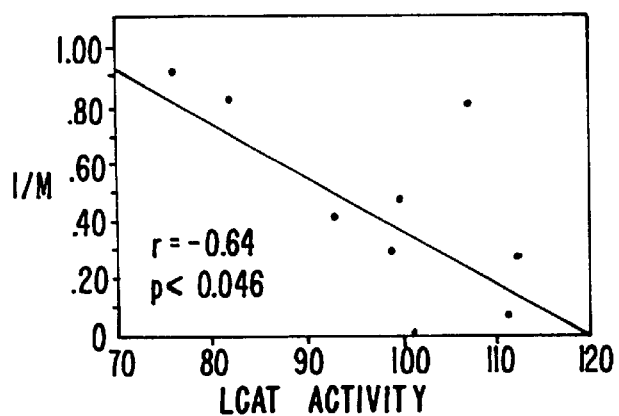
FIG. 4B: control group, showing LCAT activity in nmol/ml/h.
Figure 4C:
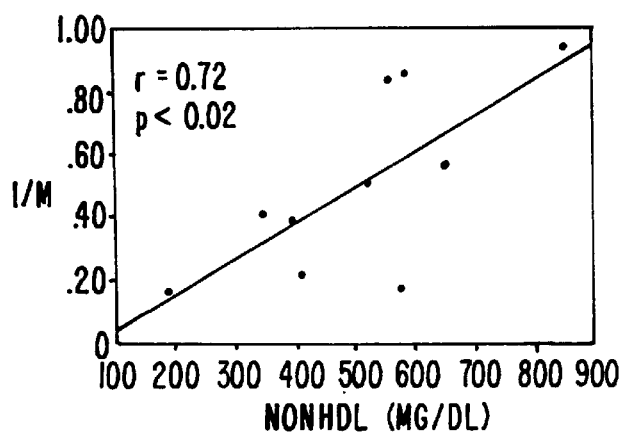
FIG. 4C: control group, showing non-HDL cholesterol, in mg/dl.
Figure 4D:
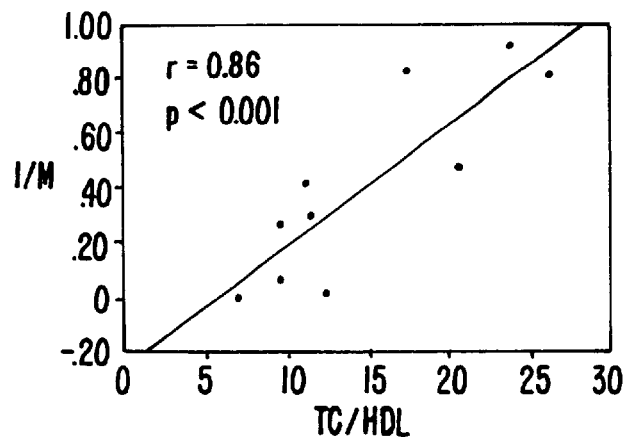
FIG. 4D: control group, showing ratio of total cholesterol to HDL cholesterol.
Figure 4E:
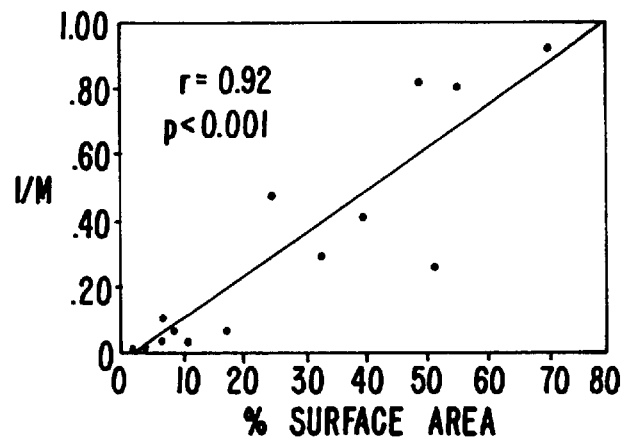
FIG. 4E: entire study group (controls and transgenics), showing % surface area.
Figure 4F:
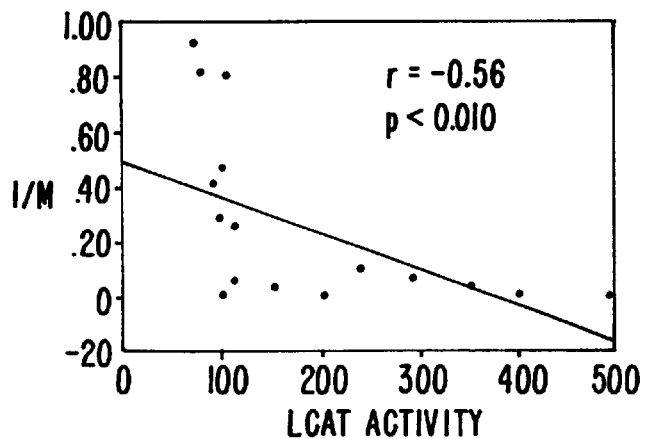
FIG. 4F: entire group, showing LCAT activity in nmol/mlh.
Figure 4G:
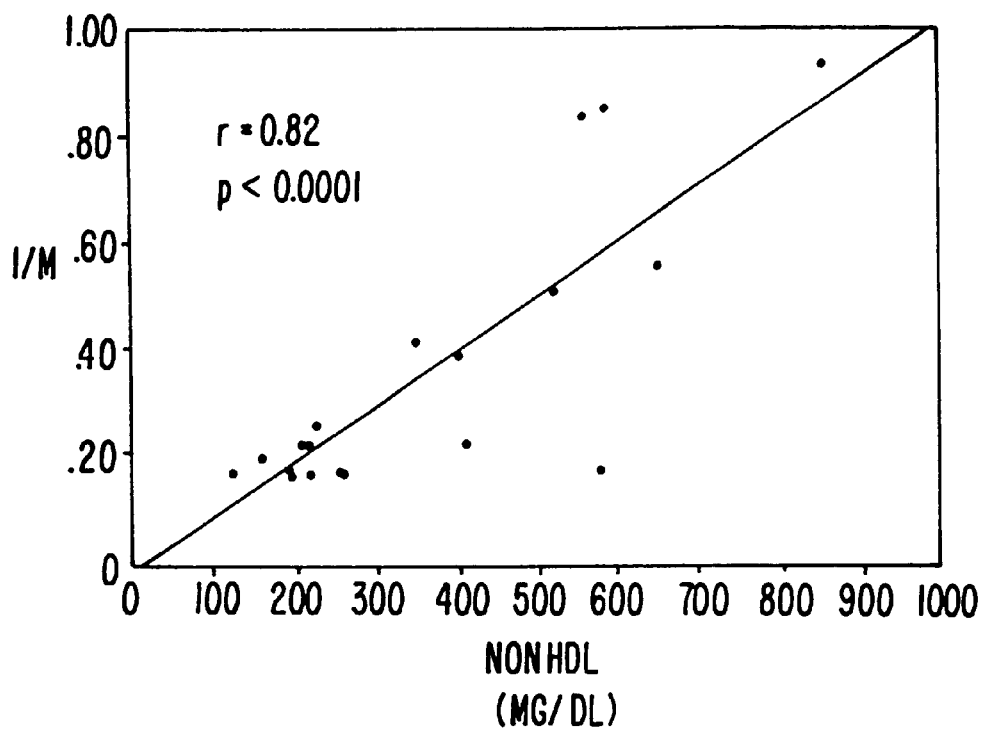
FIG. 4G: entire group, showing non-HDL cholesterol, in mg/dl.
Figure 4H:
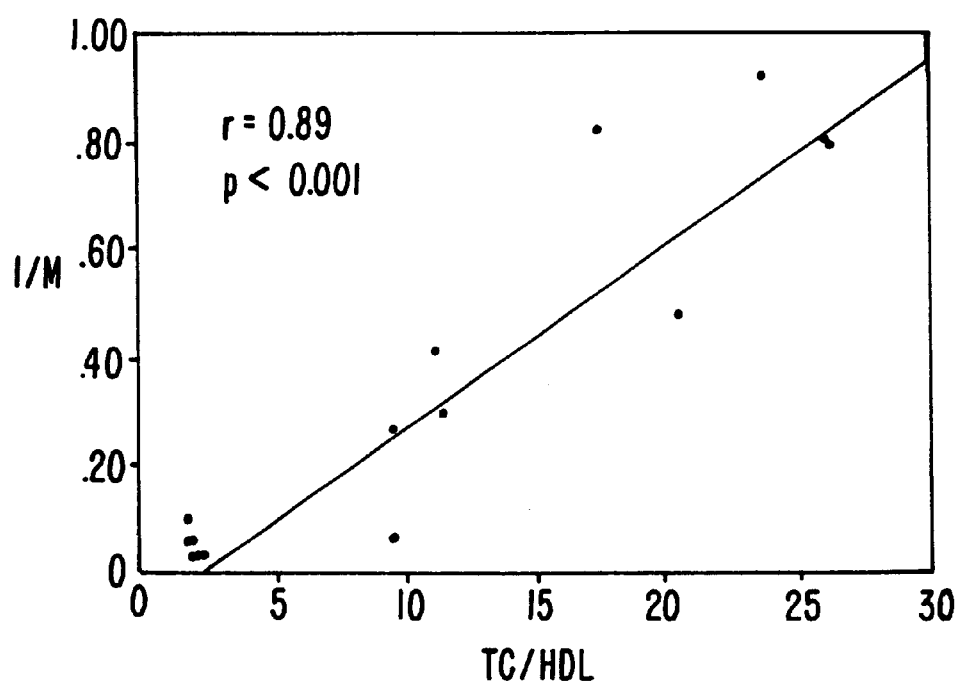
FIG. 4H: entire group, showing ratio of total cholesterol to HDL cholesterol. The intima/media ratio was inversely correlated with the severity of atherosclerosis (see FIGS. 4B and 4F) and positively correlated with the non-HDL cholesterol (see FIGS. 4C and 4G) and total cholesterol/HDL cholesterol (TC/HDL) (see FIGS. 4D and 4H).

These substantial differences in the atherosclerosis in aortae between these two groups were also evident microscopically (FIG. 2). The intima of the control rabbits demonstrated foam cell formation, cellular proliferation, and an increase in the ratio of the intima/media to 0.40±0.11 (FIG. 3, left). There was virtually no foam cell formation or cellular proliferation in the transgenic rabbits expressing human LCAT (FIG. 2). The 0.03±0.01 intima/media ratio was significantly lower than the control ($p<0.009$; FIG. 3, left). These data establish that the increase in LCAT activity led to an 85–90% reduction in atherosclerosis.

The effect of over-expression of human LCAT on atherogenesis was significantly correlated with the changes in the plasma lipoproteins. The metabolism of the atherogenic apolipoprotein B (apoB) lipoprotein particles is interrelated with that of the non-apoB associated high density lipoproteins. Patients with very high concentrations of either triglyceride-rich apoB particles (E. A. Brinton et al. (1991) *J. Clin. Invest*. 87:536) or with cholesterol-enriched LDL particles (J. R. Schaefer et al. (1992) *Arteriosclerosis and Thrombosis* 12:843) have enhanced removal of HDL particles. The interrelationship of the metabolism of these particles is at least partially mediated by the esterification by LCAT of the cholesterol present in HDL and the subsequent transfer of the cholesterol ester, by cholesterol ester transfer protein (CETP), from HDL to the apoB-containing particles. A. R. Tall (1993) *J. Lipid Res*. 34:125. Rabbits not only express more CETP than rodents and humans, but they also increase the expression of this protein with cholesterol feeding. E.M. Quinet et al. (1990) *J. Clin. Invest*. 85:357. Thus, the over-expression of LCAT in these rabbits was in the context of abundant CETP activity that affected the cholesterol concentrations of both HDL and the non-HDL particles.

To further explore the relationships among the variables relevant to lipoproteins and atherogenesis, a series of bivariate Pearson correlations were performed. The two atherosclerosis endpoints used in this study were highly correlated for both the control rabbits as well as for the entire study group (FIG. 4, pandls A and E). The severity of atherosclerosis in both the control group ($r=-0.64$, $p<0.006$; FIG. 2, panel B) and the entire study group ($r=-0.55$, $p=0.019$; FIG. 4, panel F) was inversely related to the baseline LCAT activity. These inverse correlations with LCAT activity were complemented by the significant direct correlations of both the non-HDL (FIG. 4, panels C and G) and the total cholesterol/HDL cholesterol ratio (FIG. 4, panels D and H). These dose-response relationships strengthen the association between atherogenesis and the level of LCAT expression in the control as well as in the LCAT transgenic rabbits.

There are several causes for elevated concentrations of HDL cholesterol (hyperalphalipoproteinemia) and depressed concentrations of HDL cholesterol (hypoalphalipoproteinemia). The underlying etiology leading to these different phenotypes may have different affects on atherogenesis. Although HDL cholesterol concentrations are principally determined by the clearance of HDL from the circulation (E. A. Brinton et al. (1994) *Arterioscler. Thromb.* 14:707; D. J. Radar et al., in *High Density Lipoproteins: Physiopathology and Clinical Relevance*, A. L. Catapano, F. Bemini and A. Corsini, Eds. (Raven Press, Ltd., New York, 1993), p. 43), over-production of apoA-I can lead to hyperalphalipoproteinemia (D. J. Rader et al. (1993) *Metabolism* 42:1429) and protect against the development of atherosclerosis (E. M. Rubin et al. (1991) *Nature* 353:265). In addition, HDLs represent an array of heterogeneous particles. In man, the HDL-containing apoA-I (LpA-I) has been proposed to be more effective in reverse cholesterol transport than particles containing both apoA-I and apoA-II. R. Barbaras et al. (1988) *Adv. Exp. Med. Biol.* 243:271; J. C. Fruchart and G. Ailhaud (1992) *Clinical Chemistry* 38:793; H. B. Brewer, Jr. et al., in *Disorders of HDL*, L. A. Carlson, Ed. (Smith-Gordon, 1990), p. 51. ApoA-I is a potent cofactor enhancing LCAT activity, and the modulation of LpA-I size is sensitive to the presence of apoB-containing particles and LCAT activity. M. C. Cheung and A. C. Wolf (1989) *J. Lipid Res.* 30:499. Rabbits express no apoA-II (A. L. Borresen (1976) *J. Immunogenet.* 3:73; A. L. Borresen (1976) *J. Immunogenet.* 3:83; A. L. Borresen (1976) *J. Immunogenet.* 3:91), and these transgenic rabbits have only LpA-I particles. Over-expression of LCAT in these animals may have led to the generation of an anti-atherogenic HDL subspecies.

Transgenic Mice Expressing Human LCAT

The mouse, unlike the rabbit, is not an ideal model system for human atherosclerosis. One reason for this is that lipoprotein metabolism in the mouse is significantly different than that of rabbits, humans and other non-human primates. A key metabolic difference between rabbits and mice is the presence of cholesteryl ester transfer protein ("CETP") in rabbits but not in mice. CETP mediates the transfer of cholesteryl esters from HDL to apo-B containing lipoproteins in rabbits, but not in mice. CETP mediates the transfer of cholesteryl esters from HDL to apo-B containing proteins, which facilitates delivery of cholesterol to the liver.

The effect of human LCAT expression on mice fed a high cholesterol diet was tested. LCAT expression was effected by producing transgenic mice. Transgenic mice were made by microinjection of a 6.2 kb genomic fragment of the entire human LCAT gene into fertilized eggs. See Vaisman et al. (1995) *J. Biol. Chem.* 270:12269.

Transgenic mice fed a diet high in cholesterol showed increased plasma total cholesterol, cholesteryl ester and apo-B-containing non-HDL lipoprotein concentrations, as did control animals. However, compared to controls, increased plasma total cholesterol and cholesteryl ester levels in LCAT transgenic mice reflected primarily higher plasma HDL concentrations, since the pro-atherogenic plasma non-HDL lipoproteins did not significantly differ between the two groups.

Despite relatively normal efflux of membrane cellular cholesterol, as well as the persistence of higher HDL plasma concentrations in response to the atherogenic diet, mice over-expressing human LCAT had enhanced atherosclerosis with increases in the mean aortic lesion size compared to controls, and in contrast to transgenic rabbits, a model system for human atherosclerosis.

Increased HDL levels in humans are associated with a decreased risk of cardiovascular disease. These results show that the mechanism by which HDL is increased determines the anti-atherogenic properties of the lipoprotein. Therefore, increasing LCAT activity is likely to be most effective in mammals having similar lipoprotein metabolism as humans (e.g., rabbits and non-human primates) and in humans whose lipoprotein metabolism (aside from LCAT deficiency) is relatively normal (e.g., not having CETP deficiency).

The present invention provides a novel method for use in the prophylactic or therapeutic treatment of atherosclerosis. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

TABLE 1

M2 and M16 culture media for preimplantation embryos
(From Landel, supra.)

I. Recipe for 100 ml each concentrated stock solutions.
Make all solutions using sterile disposable plasticware
and double-distilled or MilliQ water. Store at −20° C.

| Stock A | 5.534 g NaCl |
| | 0.356 g KCl |
| | 0.162 g $KH_2PO_4$ |
| | 0.293 g $MgSO_4 \cdot 7H_2O$ |
| | 2.610 g sodium lactate |
| | 1.0 g glucose |
| | 0.060 g penicillin |
| | 0.050 g streptomycin |
| Stock B | 2.101 g phenol red |
| | 0.010 g $NaHCO_3$ |
| Stock C | 0.360 g sodium pyruvate |
| Stock D | 2.252 g $CaCl_2 \cdot 2H_2O$ |
| Stock E | 5.958 g HEPES |
| | 0.010 g phenol red |

II. Preparation of 1X, M2 and M16 from concentrated stocks.
Again, use sterile plastic ware and very pure water. Mix
components gently (do not shake when dissolving BSA, as
it will foam), filter through a 0.45-$\mu$m filter, and store
4° C. for up to 1 week.

| Stock | M2 | M16 |
|---|---|---|
| A | 1.0 ml | 1.0 ml |
| B | 0.16 ml | 1.0 ml |
| C | 0.10 ml | 0.10 ml |
| D | 0.10 ml | 0.10 ml |
| E | 0.84 ml | — |
| $H_2O$ | 7.8 ml | 7.8 ml |
| BSA | 40 mg | 40 mg |

TABLE 2

CONTROL AND LCAT ACTIVITIES AND PLASMA LIPOPROTEINS
BEFORE AND AFTER CHOLESTEROL FEEDING

| | LCAT ACTIVITY (nmol/ml/h) | Total Cholesterol | Total Triglyceride | High Density Lipoprotein (mg/dl) | Non-High Density Lipoprotein | Total Cholesterol/ High Density Lipoprotein |
|---|---|---|---|---|---|---|
| Control (n = 9) | | | | | | |
| Baseline | 101 ± 11 | 29 ± 3 | 39 ± 4 | 24 ± 1 | 4 ± 3 | 1.17 ± 0.12 |
| Cholesterol-fed | 98 ± 4 | 548 ± 57* | 107 ± 15* | 39 ± 3* | 509 ± 57* | 14.98 ± 2.13* |
| LCAT-Transgenic (n = 10) | | | | | | |
| Baseline | 1593 ± 101** | 179 ± 7** | 43 ± 4 | 161 ± 5** | 18 ± 4 | 1.11 ± 0.02 |
| Cholesterol-fed | 308 ± 35* | 396 ± 33* | 81 ± 8* | 200 ± 21* | 196 ± 14* | 2.03 ± 0.07* |

From 5–7 ml of blood was drawn on rabbits after a 12 hour fast before (baseline) and after feeding a 0.3% cholesterol-chow diet (cholesterol-fed).
α-LCAT activity was determined using 10 $\mu$l of plasma in a proteoliposome assay {{46885}}.
EDTA plasma was analyzed for total cholesterol and triglyceride concentrations (Sigma, St. Louis, MO) on a Hitachi 911 Autoanalyzer (Boehringer-Mannheim, Indianapolis, IN).
The HDL cholesterol concentration was determined on plasma that had been diluted with phosphate buffered saline 1:1 (v/v) and then precipitated with dextran sulfate {{15590}}.
The total plasma cholesterol concentration, and the non-HDL cholesterol concentration was determined by subtracting the HDL cholesterol concentration from the total cholesterol concentration.
*Differs from Baseline, $p < 0.05$;
**Differs from Control Values, $p < 0.05$

What is claimed is:

1. A method for decreasing accumulation of cholesterol in arteries in a human subject not suffering from a lecithin:cholesterol acyltransferase ("LCAT") deficiency syndrome comprising administering systemically to the subject a pharmaceutical composition comprising a pharmaceutically acceptable carrier and an amount of LCAT polypeptide effective to decrease the accumulation of cholesterol in arteries of the subject.

2. The method of claim 1 wherein the pharmaceutical composition is administered parenterally.

3. The method of claim 1 wherein the pharmaceutical composition is administered by injection.

4. The method of claim 1 wherein the pharmaceutical composition is administered transmucosally or transdermally.

5. The method of claim 1 wherein the pharmaceutical composition is delivered as a unit dosage form.

6. The method of claim 5 wherein the unit dosage has about 10 mg to about 1000 mg of LCAT enzyme.

7. The method of claim 6 wherein the unit dosage form has about 40 mg to about 200 mg of LCAT enzyme.

8. The method of claim 1 wherein the LCAT is recombinant human LCAT.

* * * * *